(12) United States Patent
Wheeler

(10) Patent No.: US 7,043,371 B2
(45) Date of Patent: May 9, 2006

(54) METHOD FOR SEARCH BASED CHARACTER OPTIMIZATION

(75) Inventor: Ward C. Wheeler, Easton, CT (US)

(73) Assignee: American Museum of Natural History, New York, NY (US)

( * ) Notice: Subject to any disclaimer, the term of this patent is extended or adjusted under 35 U.S.C. 154(b) by 230 days.

(21) Appl. No.: 10/222,336

(22) Filed: Aug. 16, 2002

(65) Prior Publication Data

US 2004/0096827 A1    May 20, 2004

(51) Int. Cl.
*G06F 17/00*    (2006.01)

(52) U.S. Cl. .......................................... 702/19; 702/20

(58) Field of Classification Search .................. 702/19, 702/20
See application file for complete search history.

(56) References Cited

OTHER PUBLICATIONS

Mount, D.W., Bioinformatics—Sequence and Genome Analysis, Mar. 15, 2001, Mount, Cold Spring Harbor Laboratory Press, pp. 19-137.*

Ward Wheeler, "Alignment characters, dynamic programming and heuristic solutions", R. DeSalle, B. Schierwater (eds) Molecular Approaches to Ecology and Evolution (1998), pp. 243-251.

Ward Wheeler, "Fixed Character States and the Optimization of Molecular Sequence Data", 15 Cladistics; 379-385 (1999).

Ward Wheeler, "Homology and the Optimization of DNA Sequence Data", 17 Cladstics; S3-S11 (2001).

Aloysius Phillips, Daniel Janies, and Ward Wheeler, "Multiple Sequence Alignment in Phylogenetic Analysis", 16 Mol. Phyl. and Evol., 317-330 (2000).

Ward Wheeler, "Optimization Alignment: The End of Multiple Sequence Alignment in Phylogenetics?", 12 Cladistics, 1-9 (1996).

Daniel Janies and Ward Wheeler, "Poy Documentation Binaries Update Nov. 30, 2000", (2000).

Wheeler, et al., "The Phylogeny of the Extant Hexapod Orders", 17 Cladistics, 113-169 (2001).

* cited by examiner

*Primary Examiner*—James Martinell
(74) *Attorney, Agent, or Firm*—Davidson Davidson & Kappel, LLC

(57) ABSTRACT

A method for selecting a sequence is provided. A set of sequences are defined, each one of the sequences comprising one or more characters. A sub-set of the set of sequences are evaluated with a dynamic programing method to obtain a numeric indicia of merit. Additional sequences are added into the sub-set of sequences. The steps of defining, evaluating, and adding are repeated until the numeric indicia is substantially constant or there are no more additional sequences. One or more of the sequences are selected based on the numeric indicia.

40 Claims, 22 Drawing Sheets a

1 AAATTT b

1 ATATATATAT (SEQ ID NO: 1)

c

1 TATAT d

1 ATAGATACTAAA (SEQ ID NO: 2)

e

1 TTTAAA f

1 TTGACATAGCA (SEQ ID NO: 3)

g

1 TA h

1 GGGACCC i

1 AAA

FIG. 9

| | | |
|---|---|---|
| AAA | GGACAC | ATGATATATAA (SEQ ID NO: 24) |
| TATATA | GTAAAC | GTAATAT |
| GATATA | TAAAT | AAATTT |
| AGGTAGC | AAAAT | GATTT |
| TTAGATAGCA (SEQ ID NO: 3) | TTTATAAC | GGTTGAAC |
| ATAGATATAA (SEQ ID NO: 5) | TTATATAGC | AGATATAAC |
| TATAAA | ATATATATAC (SEQ ID NO: 13) | TAGATATAACA (SEQ ID NO: 25) |
| TTTAAA | ATAGATACTAA (SEQ ID NO: 14) | TAATAA |
| TGATATA | ATACATATAT (SEQ ID NO: 15) | TGGGATC |
| TAGAAAGC | ATAAAA | ATGATATAC |
| GGAAACC | GAGACAA | GATATAC |
| ATATATC | ATGATACTAAA (SEQ ID NO: 16) | AGAGATATAA (SEQ ID NO: 26) |
| TTATATATCA (SEQ ID NO: 6) | ATGATATAAAA (SEQ ID NO: 17) | TGAGATATCA (SEQ ID NO: 27) |
| ATATATATAA (SEQ ID NO: 7) | TATATAA | GATATCA |
| ATATAT | TGTATAA | ATATAA |
| TATAT | TATATAT | TTAAA |
| ATA | TTATATATC | TTATT |
| ATATATACTAAA (SEQ ID NO: 8) | ATATATATAT (SEQ ID NO: 18) | GAGAT |
| ATAAAT | TTACATATCT (SEQ ID NO: 19) | GGGAACC |
| TAATAT | TTAGATATCT (SEQ ID NO: 20) | ATAGATATC |
| TATTAT | GATATCT | ATGATATATCA (SEQ ID NO: 28) |
| TTGACATAGAA (SEQ ID NO: 9) | GATACAA | GATAA |
| TTAGATATAT (SEQ ID NO: 10) | ATGATATAGAA (SEQ ID NO: 21) | GGGAAA |
| GATATAT | TATAAT | ATATATAAA |
| TAAAA | TTGATATAA | TAGATATTAAA (SEQ ID NO: 29) |
| ATAGATATAT (SEQ ID NO: 11) | TTGACATAA | AAATAT |
| TTATAT | TTGACAA | AATAT |
| TGATAT | TAGACATAA | GTGTAAC |
| TAGAGATC | TAGACAA | AA |
| ATAGATATCA (SEQ ID NO: 12) | TAAAAT | ATACATATAA (SEQ ID NO: 30) |
| GATATAA | TGTTGAAA | TAA |
| GTTTATA | TGATATAAA | TATA |
| TATAA | TTGATATTAAA (SEQ ID NO: 22) | |
| ATATATATA | ATAGATACTAAA (SEQ ID NO: 23) | |

FIG. 10 a

1 ATAGATACTAAA (SEQ ID NO: 2)

b

1 TA c

1 TTGACATAGCA (SEQ ID NO: 3)

d

1 AAA e

1 GGGACCC f

1 TTTAAA g

1 ATATATATAT   (SEQ ID NO: 1)

h

1 TATAT i

1 AAATTT

FIG. 11

```
Input file format:
Americhernus    (SEQ ID NO: 34)
    1 TCGAGCCTCC AATGATACGT TGAAAGGCGT TTATCGTTGG GGCCGACAGC GCGTCGTGGG
   61 CTCGGTTGGC CTTAAAAAGC TGATCGGGTT CTCCGGCAAT TTTACTTTGA AAAAATTAGG
  121 GTGCTCAAAG CAGGCCTGGT GCC Chanbria    (SEQ ID NO: 35)
    1 TCTAGACTGG TGGTCCGCCT CTGGTGGTTA CTACCTGGCC TAAACAATTT GCCGGTTTTC
   61 CCTTGGTGCT CTTCACCGAG TGTCTTGGGG GACTGGTACG TTTACTTTGA AGAAACTAGA
  121 GTGCTCAAAG CAGGCGTAAC GCC Gea    (SEQ ID NO: 36)
    1 TCCGGCCGGA CGGGTCCGCC TACCGGTGGT TACTGTTCGC TGCCGAGCTT CAGGGGGCCG
   61 CTGTCGATGA TCTTCATCGG TTATCTTCCG TAACCCTCAC GTTTACTTTG AAAAAATTAG
  121 AGTGCTCAAA GCAGCGCGAC GCC Hypochilus    (SEQ ID NO: 37)
    1 TCCAGACGGG CGGTCCGCCT AACGGTGGTT ACTGCCTGGC CTGAACAACC AGCCGGTTTC
   61 CCTAGATGAT CTTCATTGAT TGTCTTGGGT GACCGGCACG TTTACTTTGA AAAAATTAGA
  121 GTGCTCAAAG CAGCGTGACG CC Thelichoris    (SEQ ID NO: 38)
    1 TCCAGACGGG CGGTCCGCCT AACGGTGGTT ACTGCCTGGC CTGAACAGCC AGCCGGTTTC
   61 CCTAGATGAT CTTTACCGGT TGTCTTGGGT GACCGGCACG TTTACTTTGA AAAAATTAGA
  121 GTGCTCAAAG CAGGCTGACG CC Amblypygid    (SEQ ID NO: 39)
    1 TCCAGACTGG CGGTCCGCCT AGCGGCGAGT ACTGTCAGGC CTGAACATGG CGCCGGTTTT
   61 CCTTGGTTCT CTTTACTGAG TGTCTTGGGC GACCGGCACG TTTACTTTGA AAAAATTAGA
  121 GTGCTCAAAG CAGGCTGTCG CC Mastigoproctus    (SEQ ID NO: 40)
    1 TCCAGACGGG TGGTCCACCG CCCGGTGGCT ACTGCCCGGC CTGAACAATC TCGCCGGTTT
   61 TCCTTGATTC TCTTCACCGA GTGTCTTGGG TGACCGGCAC GTTTACTTTG AAAAAATTAG
  121 AGTGCTTAAA GCAGCGTAAC GCC Rhiphicephalus    (SEQ ID NO: 41)
    1 TCCAGACGAG TAGTGCATCT ACCCGATGCT ACGGCTCGGA CTGAACATCA TGCCGGTTCT
   61 TTCTTGGTGC ACTTCATTGT GTGCCTCGAG ATGGCCGGTG CTTTTACTTT GAAAAAATTA
  121 GAGTGCTCAA CGCAGGCGAG TCGCC Vonones    (SEQ ID NO: 42)
    1 TCGAGGCTGG CGGTCCGCCT ACAGGCGGTC ACTGCCAGTA CTCAACATCC TGCCGGTTTT
   61 CCCTTGGTGC TCTTCGCTGA GTGTCTCGGG TGGCCGGCAC GTTTACTTTG AAAAAATTAG
  121 AGTGCTCAAA GCAGGCGCGT AGCC Centruoides    (SEQ ID NO: 43)
    1 TCCAGACAAG CGGTCCACCC GCGGTGGTTA CTGTTTGGAC TGGACGTTTG GCCGGATTCC
   61 TTTGATGCTC TTTGCCGAGT GTCTTGGGTG TCCGGCACGT TTACTTTGAA AAAATTAGAG
  121 TGCTCAAAGC AGCGTACCGC C Hadrurus    (SEQ ID NO: 44)
    1 TCCGGACTGT CGGTCCGCCC AAGCTTACT GGCAGGACCG GACGTCTAGC CGGACTCTCT
   61 CGTATCCTCT TCACCGGGTG TCTTGGGTGT CCGGCAATTT TACTTTGAAA AATTAGAGT
  121 GCTCAAAGCA GCGCGATCCG CC Pauroctonus
```

FIG. 16

OUTPUT:

(AMERICHERNUS (((((((CHANBRIA LIMULUS) (CENTRUOIDES (HADRURUS PAUROCTONUS))) MASTIGOPROCTUS) (AMBLYPYGID ((RHIPHICEPHALUS VONONES) ((APORTUS ALENTUS) THERMOBIUS)))) HYPOCHILUS) THELICHORIS) GEA) ARTEMIA))[387]
;
  BINARY REPRESENTATIONS OF BEST TREES:
(AMERICHERNUS (((THELICHORIS (((((LIMULUS CHANBRIA) (CENTRUOIDES (PAUROCTONUS HADRURUS))) MASTIGOPROCTUS) (((THERMOBIUS (ALENTUS APORTUS)) (VONONES RHIPHICEPHALUS)) AMBLYPYGID)) HYPOCHILUS)) GEA) ARTEMIA))[387]
;

TREE 0
_ AMERICHERNUS
|__ ARTEMIA
  |__ GEA
   |__ THELICHORIS
    |__ HYPOCHILUS
     |_____ AMBLYPYGID
      | |_____ RHIPHICEPHALUS
      | | |_ VONONES
      | |___ THERMOBIUS
      |   |__ ALENTUS
      |   |_ APORTUS
      |__ MASTIGOPROCTUS
       |_____ CHANBRIA
        | |_ LIMULUS
        |___ CENTRUOIDES
         |__ HADRURUS
          |_ PAUROCTONUS

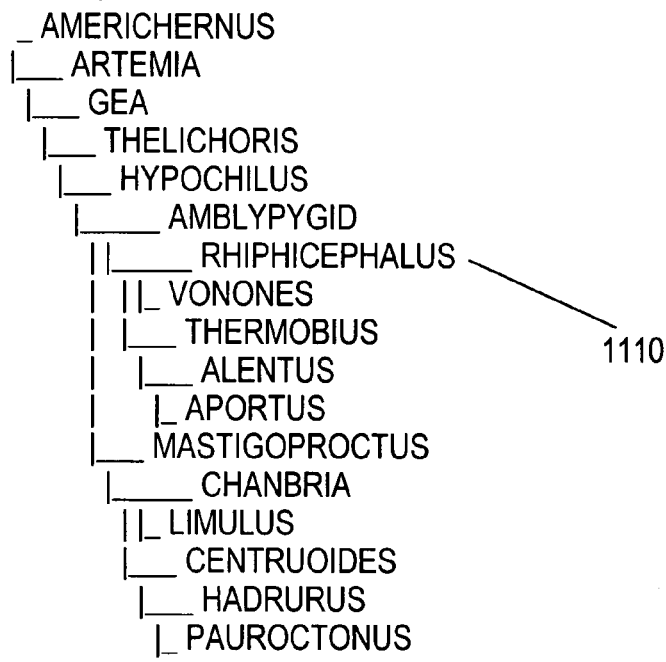

METHOD FOR SEARCH BASED CHARACTER OPTIMIZATION

BACKGROUND INFORMATION

The advances of molecular biology have made possible the comparative study of proteins and the nucleic acids (DNA and RNA), which are repositories of hereditary (evolutionary and developmental) information. Nucleic acids and proteins are linear molecules made up of sequences of units—nucleotides in the case of nucleic acids, amino acids in the case of proteins—which retain considerable amounts of evolutionary information. By comparing two nucleic acids or proteins with one another, the number of their units that are different can be established. For example, the units that are different could be DNA base changes (e.g., Adenosine to Guanine) or the insertion and/or deletion of nucleotides. The number and type of differences are indications of the recency of common ancestry. This allows comparisons to be made between very different sorts of organisms by comparing the sequences that arise in two or more sequences of nucleic acid or protein. For example, organisms as diverse as yeasts, pine trees, and human beings can be compared since there are homologous nucleic acids that can be compared in all three.

The comparisons can be used to provide information not only about the topology of evolutionary history (cladogenesis), but also about the amount of genetic change that has occurred in any given lineage (anagenesis). For example, cytochrome c (a protein molecule) of humans and chimpanzees consists of the same 104 amino acids in exactly the same order; but differs from that of rhesus monkeys by 1 amino acid, that of horses by 11 additional amino acids, and that of tuna by 21 additional amino acids. This similarity is believed to reflect the recency of common ancestry. Thus, the inferences from comparative anatomy and other disciplines concerning evolutionary history can be tested in molecular studies of DNA and proteins by examining their sequences of nucleotides and/or amino acids.

A cladogram based on parsimony can be constructed from the relationships found between the sequences (of nucleic acids or proteins) for different organisms. A cladogram based on parsimony is a branching diagram representing the distribution of derived characters within a set of taxa (units used in the science of biological classification), such that the total number of evolutionary events is minimized. In the cladogram, the type of change of one taxon to another indicates the degree of relationship; i.e., closely related groups are located on branches close to one another.

The determination of the length cost of a cladogram is known to be NP-complete (non-polynominal) when the internal nodal sequences are unknown, so that the overall cladogram length is minimized. This is understood when one contemplates the increasing number of possible sequences as the number of observed sequences increase. In principle, all possible sequences of lengths 1 to the sum of all terminals with all possible combinations of nucleotides may occur. Wang and Jiang (L. Wang & T. Jiang, *On the complexity of multiple sequence alignment*, Journal of Computational Biology 1:337–348 (1994).) discussed this in their proof of NP-completeness and Wheeler (W. C. Wheeler, *Alignment Characters, Dynamic Programming, and Heuristic Solutions, in Molecular Approaches to Ecology and Evolution* 2nd Edition 243–251, (R. DeSalle & B. Schierwater, eds., Birkhäuser Verlag, Basel Switzerland, 1998).) in terms of optimization alignment (W. C. Wheeler, *Optimization Alignment: the end of multiple sequence alignment in phylogenetics*, Cladistics 12:1–9 (1996).).

To find an exact solution, all possible sequences can be enumerated and tried at each internal node, or for example, a branch and bound method could be used. Such an approach would guarantee the optimal solution, but is a time-consuming method and requires large amounts of computational resources.

Another approach to the estimation cladogram lengths has been one of constructing a point estimate for hypothetical ancestral sequences and then using this to determine an upper-bound on cladogram length. For example, the coupled processes of multiple sequence alignment and separate phylogenetic reconstruction does this through establishing global, static homologies to deal with length variation and then using standard optimization techniques to estimate the internal node character states. Optimization alignment (W. C. Wheeler, *Optimization Alignment: the end of multiple sequence alignment in phylogenetics*, Cladistics 12:1–9 (1996).) takes a more direct (and explicit) approach to this estimation by establishing cladogram-specific homology schemes in a preliminary pass and constructing ancestral sequences in a second, up-pass. Optimization Alignment usually yields better upper bounds on minimum tree length (e.g., cladogram) than multiple alignment methods. Another method is a Fixed-Character State optimization method, which estimates internal nodal sequences by requiring they be drawn from the set defined by the terminals. In general, this yields less satisfactory cladogram lengths. In each of these procedures, a single hypothetical ancestral sequence is generated for each internal node of the cladogram. However, the procedures require large amounts of computational resources.

SUMMARY

A method for selecting a sequence is provided. A set of sequences are defined, each one of the sequences comprising one or more characters. A sub-set of the set of sequences are evaluated with a dynamic programing method to obtain a numeric indicia of merit. Additional sequences are added into the sub-set of sequences. The steps of defining, evaluating, and adding are repeated until the numeric indicia is substantially constant or there are no more additional sequences. One or more of the sequences are selected based on the numeric indicia.

A method for selecting a sequence is provided. A possible set of sequences is defined from an original set of sequences. Each one of the sequences comprises one or more characters. The possible set of sequences and the original set of sequences is evaluated with a dynamic programing method to obtain a numeric indicium of merit. One or more of the sequences are selected based on the numeric indicium.

BRIEF DESCRIPTION OF THE DRAWINGS

FIG. 9 shows 9 sequences (SEQ ID NO: 1–9) used to compare technique in accordance with an embodiment of the present invention to other methods known in the art.

FIG. 10 (SEQ ID NO: 10) shows a plurality of candidate ancestral sequences.

FIG. 11 (SEQ ID NO: 11–19) shows 9 sequences.

FIG. 16 (SEQ ID NO: 20–30) shows an input file in accordance with an embodiment of the present invention.

FIG. 17 shows the cladogram generated in accordance with an embodiment of the present invention for the input file shown in FIG. 16.

DETAILED DESCRIPTION OF THE PREFERRED EMBODIMENTS

In an embodiment according to the present invention, one or more of sequences are obtained from one or more potential organisms. A set of possible ancestral sequences (e.g., candidate sequences) are defined. Optimization Alignment, based on a Wagner Tree, can be used to generate the set of possible ancestral sequences. The set of possible ancestral sequences are then evaluated via a dynamic programing method to obtain a numeric indicium of merit (e.g., parsimony). Preferably, additional sequences are added into the set of sequences, the above steps are repeated, and one of the ancestral sequences is selected based on the numeric indicium. Preferably, additional sequences are added until stability is reached (e.g., the value of the numeric indicia remains substantially constant) or until no further sequences are available. The set of possible ancestral sequences can be defined by a plurality of Wagner trees that are constructed by random additions of the sequences into the trees. Each tree is constructed with a different random order. In an embodiment according to the present invention where the sequences obtained are nucleic acids and/or proteins of a plurality of organisms, the ancestral sequence chosen can be representative of the evolutionary history of said organisms.

Figure 1:
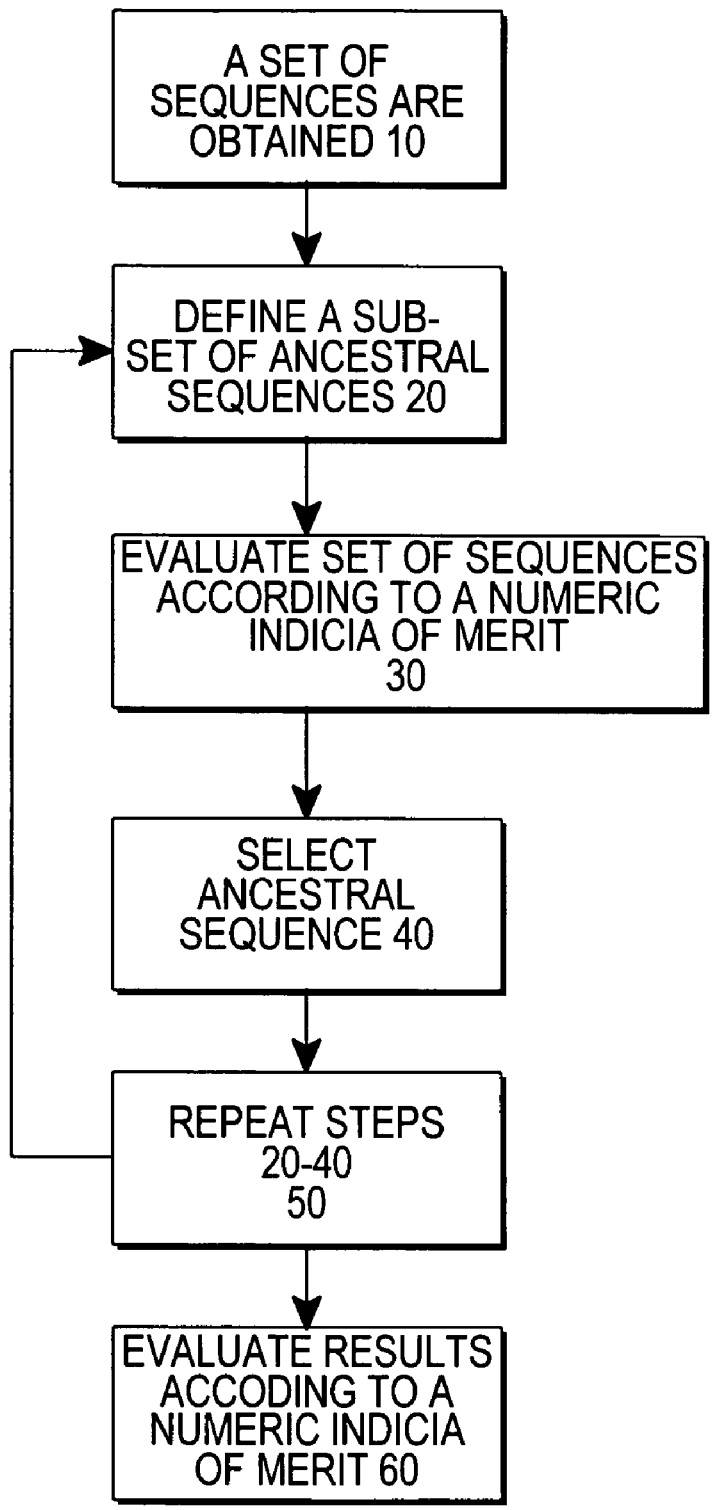
FIG. 1 shows a flow chart illustrating the process according to an embodiment of the present invention.
Figure 4:
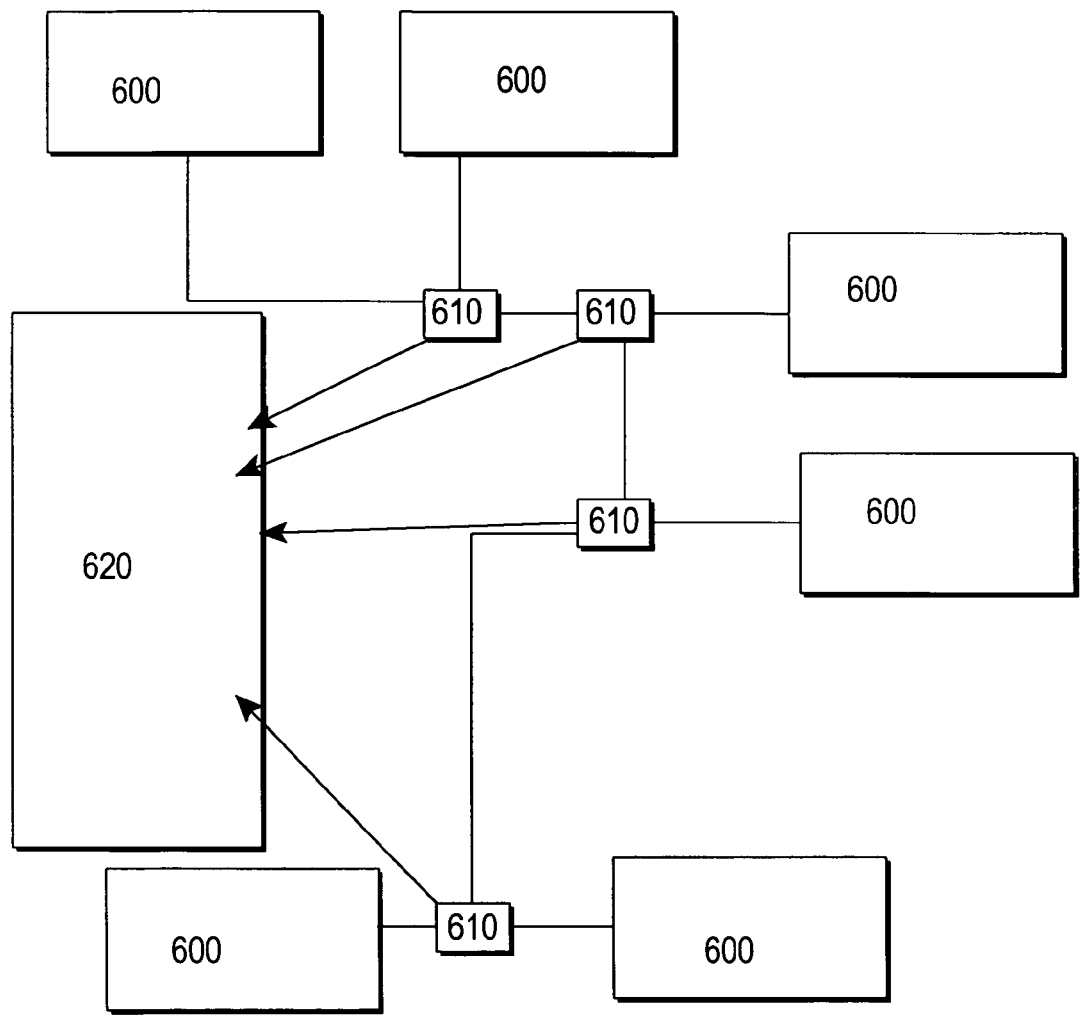
FIG. 4 shows an illustrative Wagner Tree.

FIG. 1 shows a flow chart detailing an embodiment of the present invention. A set of sequences (e.g., states) are obtained from one or more organisms (Step 10). The set of sequences can be, for example, a set of nucleotides or amino acids of a plurality of taxa (e.g., organisms). Moreover, the set of sequences could be from the same organism, for example, genetic sequences from cancer cells and non-cancerous cells. The set of sequences or a portion thereof are then used to define a set of possible ancestral sequences (Step 20). The set of possible ancestral sequences could be constructed based on a Wagner Tree (as shown in FIG. 4). The set of possible ancestral sequences are then evaluated according to a numeric indicium of merit (Step 30). Preferably, the set of possible ancestral sequences are evaluated via a dynamic programing method (discussed below FIG. 7.) Based on the evaluation, one or several of the ancestral sequences are selected (Step 40). In certain embodiments of the present invention, Steps 20–40 can be repeated with new ancestral sequences or ancestral sequences that were obtained in Step 10, but not yet used in remaining Steps 20–40 (Step 50). Then, the ancestral sequences that are selected can be evaluated until stability or exhaustion occur according to a numeric indicium of merit. (Step 60). The occurrence of stability or exhaustion is determined by the numeric indicium of merit of ancestral sequences that are selected (shown schematically in FIG. 15).

Figure 15:
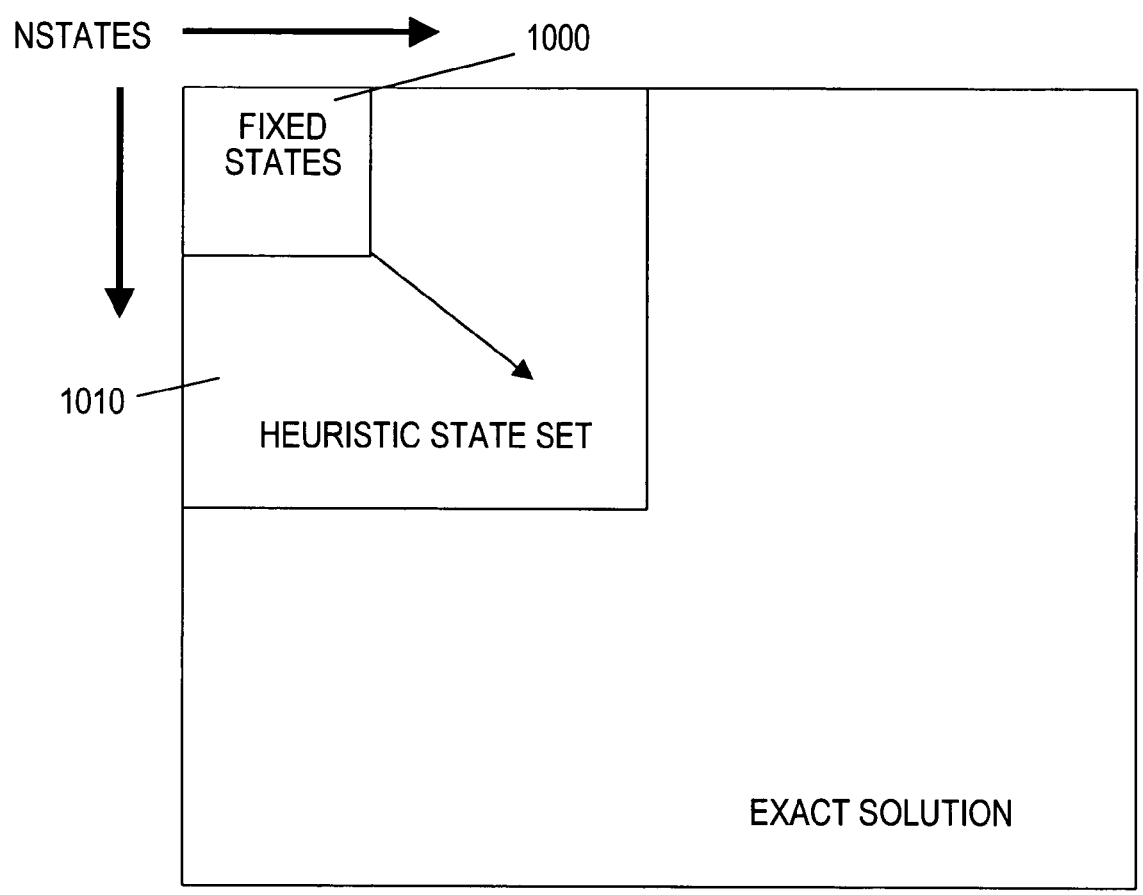
FIG. 15 shows a schematic representation of an embodiment of an enlargement of the states-set.
Figure 18:
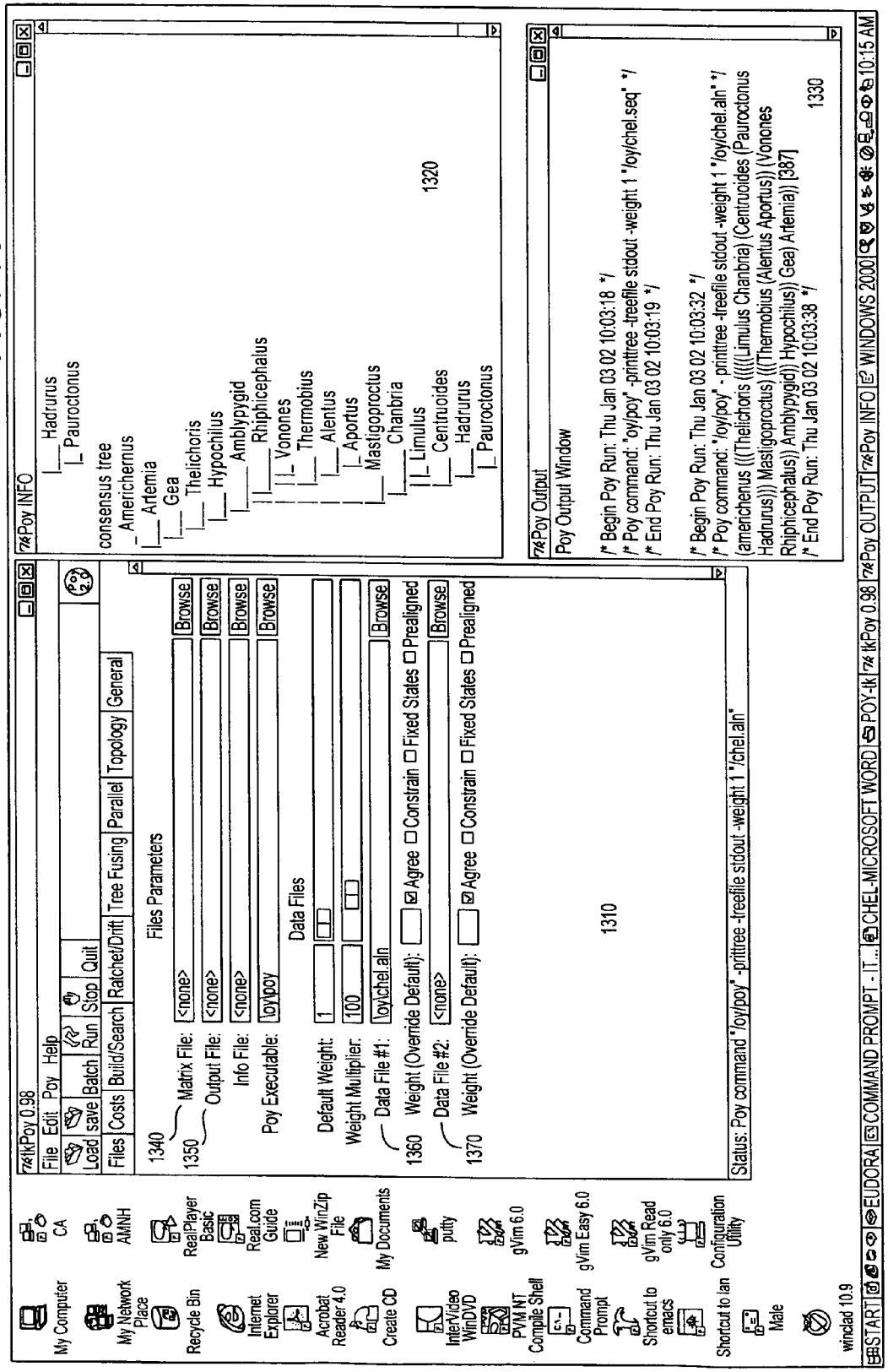
FIG. 18 shows a GUI interface in accordance with an embodiment of the present invention.

Referring to FIG. 15, Steps 20–40 are preferably first performed on a small set state (e.g., a fixed set of sequences) 1000. Based on the results obtained, the set of possible sequences can be enlarged, for example, a heuristic state set 1010, and the procedure is repeated (Step 50 in FIG. 1). This is done until stability or exhaustion (e.g., an exact solution 1020 is found) have occurred (Step 60 in FIG. 1).

Figure 2:
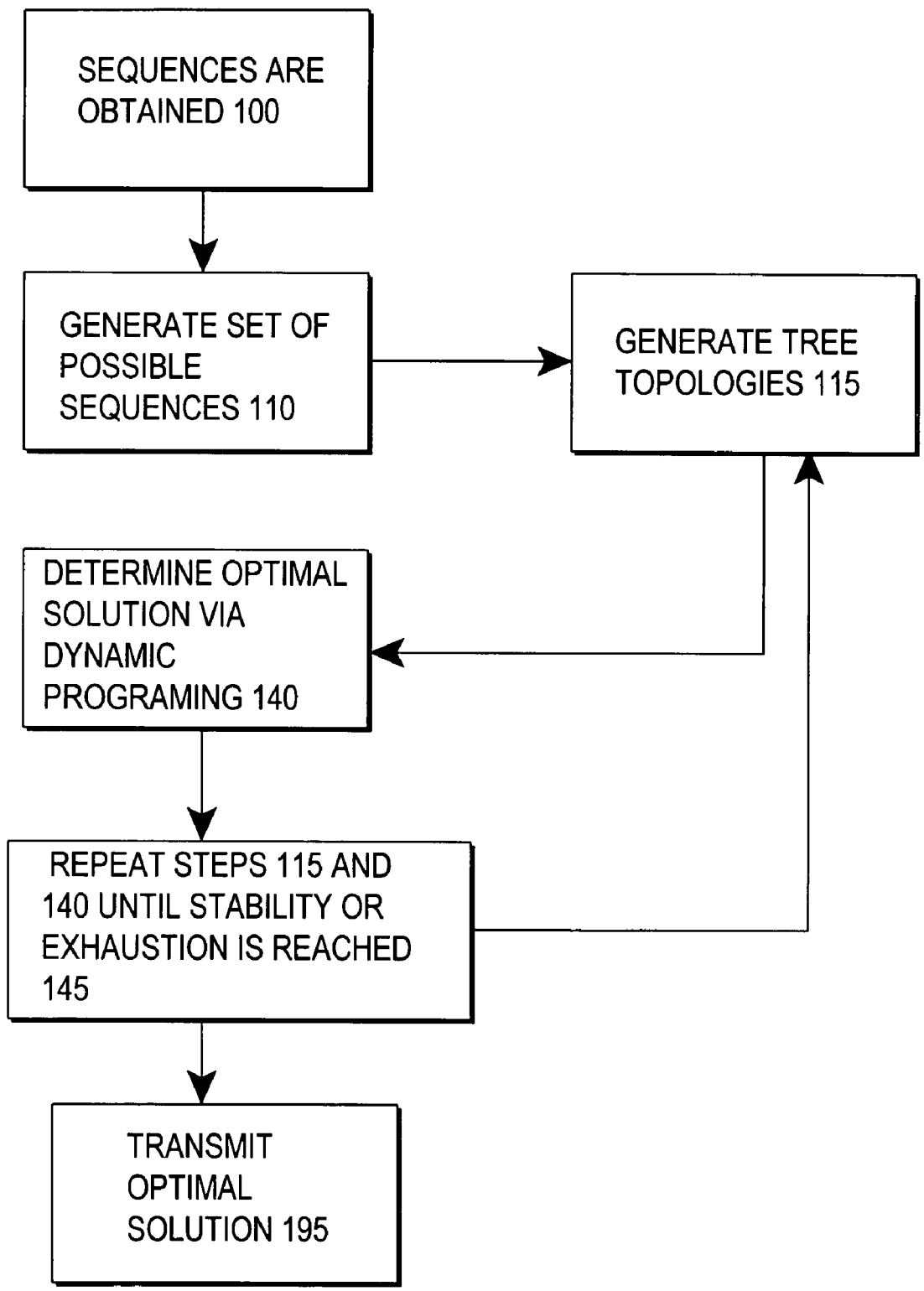
FIG. 2 shows a flow chart illustrating the process according to another embodiment of the present invention.

FIG. 2 shows a flow chart illustrating the process of another embodiment of the present invention. One or more sequences (e.g., original sequences or ancestral sequences previously generated) are obtained from a plurality of organisms (Step 100). Preferably, the original sequences are observed from databases or lab work, and ancestral sequences are hypothetical sequences in a hypothetical ancestor. It should be noted that the terms ancestral sequence, original sequence, and possible sequence are used interchangeably with the term state (but, not with each other) throughout the document. The sequences can be represented by a set of characters. In an embodiment of the present invention wherein the sequences are nucleic acid sequences, each sequence can comprise a heuristic subset. The sequences can be obtained by methods known in the art, such as prior art synthetic methods or gene databases. Preferably, the sequence set chosen such that the set is as small as possible while including as much pertinent variation as possible, since the computational cost of the dynamic programming step (below) is dependent on the square of the number (e.g., size or length) of the sequences. For example, even though sequences containing many "T"s (thymine) are possible in a problem where only "G"s (guanine) and "C"s (cytosine) are observed, it would be inefficient to include the sequences with the "T"s, because they are very unlikely to be useful.

A set of possible sequences (e.g., a heuristic state set) is then generated from the set of sequences (Step 110). Preferably, the set of possible sequences is a super-set of the ancestral sequences and/or original sequences. In certain embodiments of the present invention, Step 110 can be done by generating random sequences where the length of the random sequences is specified. For example, all the possible sequences that comprise a set of characters of length 10–15 could be generated. Preferably, optimization alignment is used to generate the set of possible sequences (shown in FIG. 3). Most preferably, the optimization alignment uses a tree based method. For example, random trees or Wagner trees can be built, and then the internal nodes of said trees added to the set of possible sequences and obtained sequences. For example, $N^4$ Wagner trees of $\Pi$ 2i–5 (i=3 to N for N taxa) could be generated. Then, the internal nodes (which are possible sequences) are extracted from the Wagner Trees and added to the set of (actual) sequences. In certain embodiments of the present invention, certain orderings can be excluded. For example, if the ancestral sequences comprise set[A–G], orderings where B and D are the roots of the trees could be excluded.

One or more topologies (e.g., trees or directed graphs) are then generated 115 based on the set of observed sequences. The set of possible sequences and/or observed sequences can be used as internal node sequences (e.g., states) of the tree. A variety of prior art methods exist for generating the tree topologies, such as the computer program POY. In certain embodiments of the present invention, tree refinement procedures, such as branch swapping, can be used to improve efficiency. In a parallel processing environment, separate processes can be spawned for each tree generation and executed in parallel.

A dynamic programing method based on each of the topologies, the set of possible sequences, and the set of observed sequences is used in order to determine a possible solution (e.g., a cladogram) (Step 140). For example, a Sankoff and Rousseau procedure where the internal nodes of the tree are the set of possible and/or observed sequences can be used. Preferably, the dynamic programing step outputs a length for each of the topologies. In a parallel processing environment, separate processes could be spawned for each tree topology and executed in parallel.

In certain embodiments of the present invention, compression of states (e.g., sequences) can be used to accelerate cladogram length calculation, since the time of the dynamic programing step is dependent on the number of states (e.g., sequences) used at the internal node. A full down-pass of a cladogram of "n" taxa and "m" states (e.g., sequences) would have a complexity on the order of $nm^2$ for each character. However, in certain embodiments of the present invention, the "n" taxa can be reduced almost to a constant factor of 2 via the shortcuts described by Goloboff (P. A. Goloboff, *Character optimization and calculation of tree lengths*, Cladistics 9:433–436 (1994) and P. A. Goloboff, *Tree searches under Sankoff parsimony*, Cladistics 14:229–237 (1998).) Moreover, since the Goloboff shortcuts are dependant on the final ancestral states (e.g., sequences) reconstructions, they can also be used to reduce $m^2$ to as low as 1 or 2. Although there can be m states (e.g., possible ancestral sequences) possible, the number of states reconstructed at the internal nodes is usually one or two. However, in such an embodiment, the length calculations are approximate and thus, are checked with a down-pass length calculation which is dependant on the full state set. In certain embodiments of the present invention, incremental optimization (an "accounting" procedure whereby a minimum of tree information is updated to reduce calculation time) can reduce the complete down-pass costs from n to log n (D. G. Gladstein, *Incremental evaluation and the diagnosis of cladograms*, Cladistics 13:21–26 (1997).) The compression of states (e.g., sequences) can occur as they are found, for example, in Step 110. Also, the compression of states can be applied to the entire set of states (e.g., sequences) before the states are used as internal nodes (e.g., before Step 140).

Steps 115 and 140 are repeated until stability exists within the set of possible solutions or until exhaustion is reached (e.g., all the possible solutions possible have been generated) (Step 145). This is shown in FIG. 15. Preferably the determination of stability is based on the lengths of the topologies.

In certain embodiments of the present invention, Step 115 can be performed before Step 110. In such an embodiment, the set of possible sequences can be enlarged and tried on the already generated tree topologies until stability or exhaustion is reached.

One or more optimal solutions are then chosen from the set of possible solutions (Step 160). Preferably, the optimal solution can be based on the lengths of the topologies that were determine in Step 140. Most preferably, the shortest length is chosen. The optimal solution can be, for example, a cladogram diagraming evolutionary relationships. In certain embodiments, the optimal solution could be the sequence of genetic changes between a normal cell and a cancerous cell.

In certain embodiments of the present invention, the optimal solutions that were selected can be transmitted (Step 195). This would allow for efficient data compression of DNA sequences. By doing so, the transmission of, for example, 100 whole genome sequences would no longer require the transmission of all the nucleotides (e.g.,100 billion). Instead, the cladogram (correct or not) relating a plurality of genomes, and the list of changes on the cladogram could be transmitted. This is because the cladogram describes the order in which genetic sequences have changed between two or more organisms.

In certain embodiments of the present invention, the number of candidate sequences examined during the search can be reduced. For example, the sequences used in intermediate solutions (e.g., during the initial cladogram building steps) can be noted and the unused sequences can be removed for an initial refinement step. For example, taxa can be added m at a time till all the taxa are added (similar to Wagner additions), then certain candidate sequences could be discarded. After the initial refinement step has completed, the sequences are returned to the state (e.g., sequence) set and the refinement step is repeated. The steps of refining and returning could be performed iteratively until stability occurred.

Figure 3:
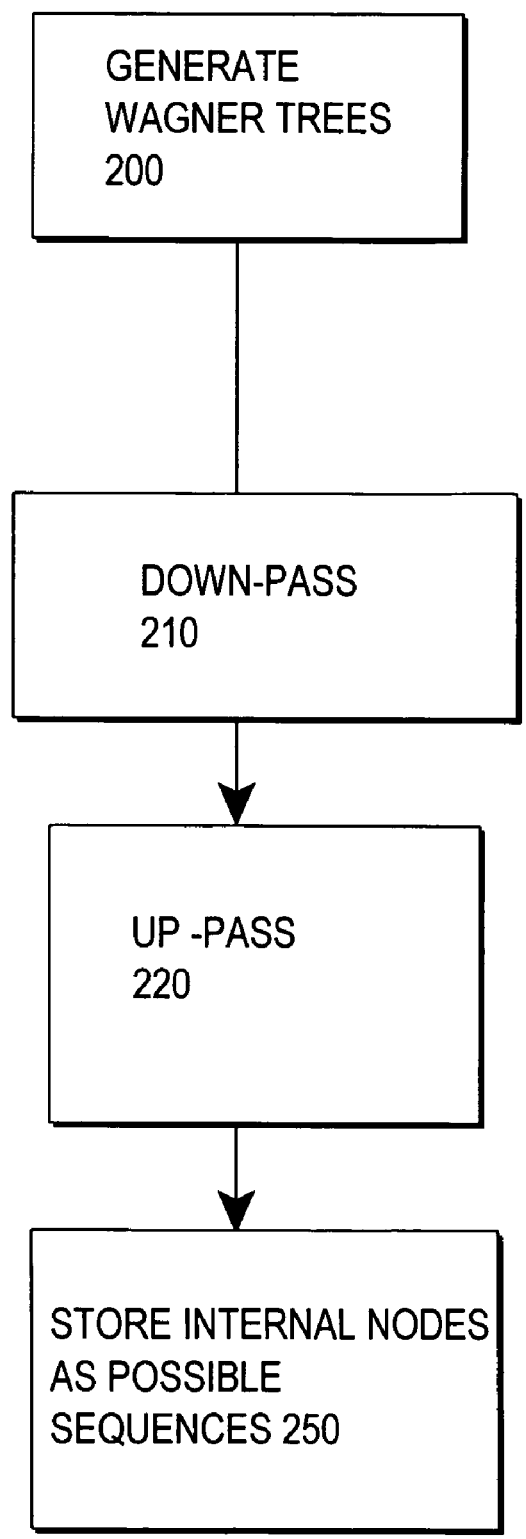
FIG. 3 shows a flow chart detailing the optimization alignment.

FIG. 3 shows a flow chart detailing the optimization alignment, which, as discussed above, is a preferred method of generating a set of ancestral sequences (e.g., Step 20 In FIG. 1 and Steps 110 and 115 in FIG. 2). In brief, Optimization Alignment (OA) is a method for taking unaligned sequences and creating parsimonious cladograms without the use of multiple alignment (W. C. Wheeler, *Optimization Alignment: Down, Up, Error, and Improvements, in Molecular Systematics and Evolution* 56–69, (R. DeSalle et al., eds., Birkhäuser Verlag, Basel Switzerland, 2001).) First, a plurality of Wagner trees are built by inserting the original sequences in a different random order for each tree (Step 200). For example, given the set of original sequences [A–D], the first random order could be [b, c, d, a] and the next random order could be [c, a, b, d]. A complete Wagner Tree is shown in FIG. 4.

In the OA method, a "down-pass" moves "down" each of the trees from the set of sequences (e.g., sequences obtained from observed taxa) to the root or base of a tree (e.g., a cladogram) (Step 210). Step 200 is shown in more detail in FIG. 5 (and discussed infra). During, the down-pass preliminary (i.e. provisional) hypothetical ancestral sequences are created at the internal nodes of the tree and the tree length is generated as a weighted sum of the character transformations (e.g., nucleotide substitutions and insertion-deletion events) required by the terminal sequences. Next, an "up-pass" moves back up from the base to the tips (Step 220). Step 210 is shown in more detail in FIG. 6 (and discussed infra). The up-pass takes the information from the down-pass and creates the "final" estimates of the hypothetical ancestral sequences. The combination of these two procedures allows phylogenetic searches to take place on unaligned sequence data, resulting in improvements in execution time and quality of results. This process differs from multiple alignment procedures, such as that of Sankoff and Cedergren (D. Sankoff & R. Cedergren, *Simultaneous comparison of three or more sequences related by a tree*, in *Time Warps, String Edits, and Macromolecules: the Theory and Practice of Sequence Comparison* 983, (D. Sankoff & J. B. Kruskal eds., 1983).) in that OA attempts to determine the most parsimonious cost of a tree directly whereas multiple alignment procedures generate column-vector character sets, which are then analyzed phylogenetically in a separate operation.

The internal nodes are then stored as possible candidate sequences (Step 250).

The OA method allows the direct optimization of unequal length sequences on a cladogram (W. C. Wheeler, *Optimization Alignment: the end of multiple sequence alignment in phylogenetics*, Cladistics, 12:1–9 (1996).) That is, the determination of the length, or cost, of the cladogram is accomplished given the observed sequences and a cost matrix that specifies the costs of all the transformations among nucleotides and insertion-deletion (indel) events.

Sankoff and Rousseau (D. D. Sankoff & P. Rousseau, *Locating the vertices of a Steiner tree in arbitrary space*, Math. Prog. 9:240–246 (1975).) expanded the realm of optimization allowing for unequal transformation costs among character states, but still relied on a preexisting alignment to know which states to compare. OA enlarges the world of transformation events that can be optimized on a cladogram, including the creation and destruction of characters. In doing this, OA obviates the need to perform multiple sequence alignment, creating unique, topology specific homology regimes for each scenario of historical relationship. This yields better testing of phylogenetic hypotheses since provisional homologies are optimized for each cladogram individually, not a priori and universally as with the static homologies of multiple alignment. Furthermore, by treating all sequence variation within the context of topology-specific synapomorphy, hypotheses of molecular variation can be seamlessly integrated with other character variation to yield simultaneous or total evidence analysis. The OA integration of molecular and other character information frequently generates more parsimonious cladograms than multiple sequence alignment (W. C. Wheeler, *Homology and the Optimization of DNA Sequence Da*, Cladistics, 17: S3–S11 (2000).) and these results often show greater congruence among data sets (G. Giribet, *Exploring the Behavior of POY, a Program for Direct Optimization of Molecular Data*, Cladistics, 17: S60–S70 (2001).)

Preferably, multiple solutions, sub-optimal solutions, and character-specific virtual roots are used to augment the procedure.

Multiple solutions can be applied during the down-pass and the up-pass. During the down-pass, consideration of multiple equally parsimonious preliminary sequences can be used. Since each node likely would generate its own multiple solutions which should be multiplied down the cladogram, extremely large potential sets of preliminary sequences could be generated. Although it might not be practical to maintain multiple solutions throughout the entire down-pass, these solutions (or a set of them) could be maintained and considered at the determination of the next (parent) node (or some other range down the cladogram). The NW-HSC (Needlemen Wusch Heuristic Sankoff Cost) process could be performed on each combination of the candidate preliminary sequences for the two descendants of a node. This would generate a new set of equally costly preliminary sequences for this node and the process would be repeated until the entire cladogram was optimized.

The up-pass determination of the final hypothetical ancestral sequences could also be improved by maintaining multiple equal cost solutions. Here, there would be the product of the multiple preliminary solutions and those of the final assignment of the parent node, which would be more computationally intensive, but surely tractable. The same decisions on the size of the set of solutions to be maintained (this could be large, or a smaller random sample could be stored) and the reach over which to hold and test these multiple solutions would be required.

Figure 19:
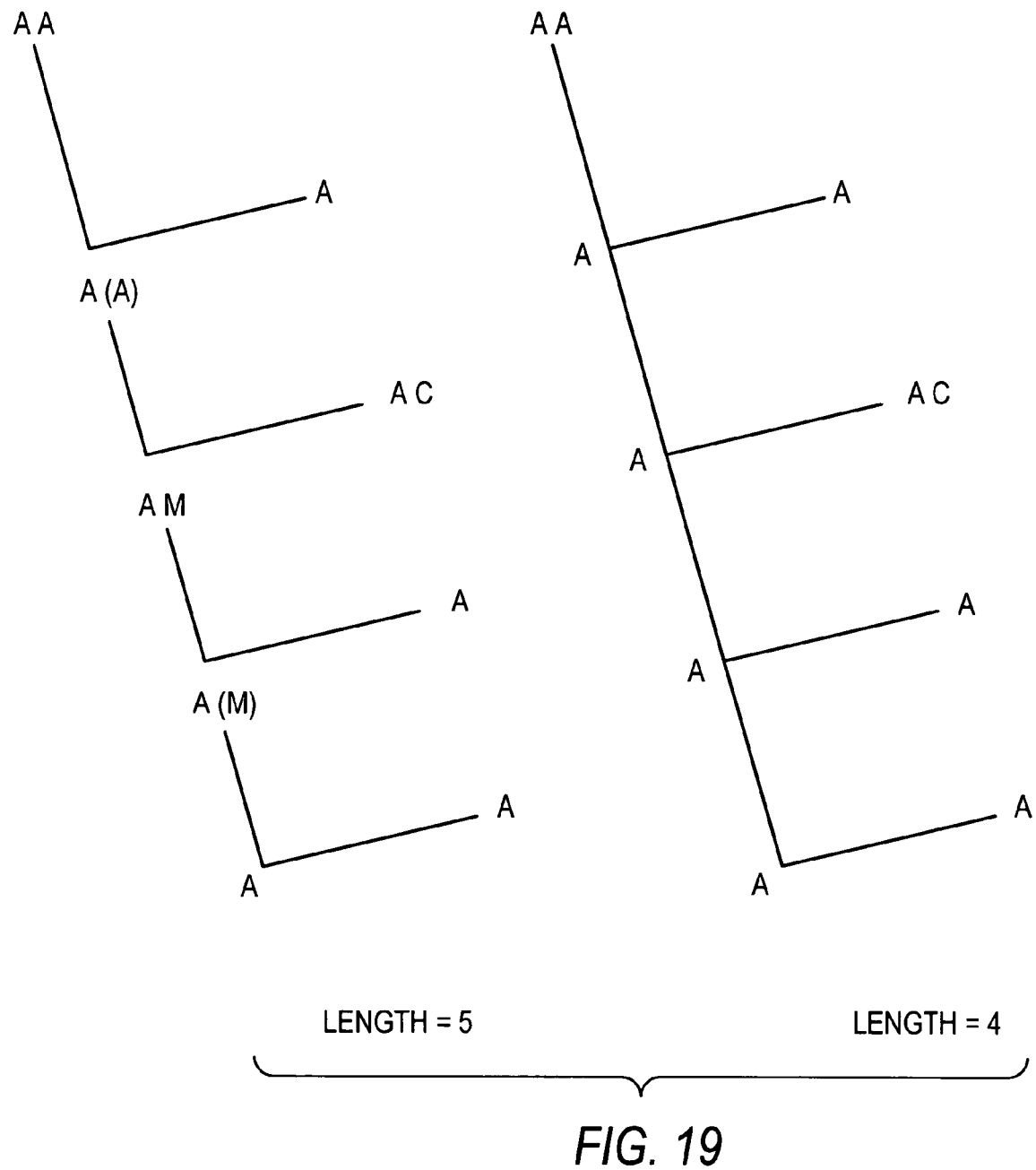
FIG. 19 illustrates an a preliminary sequence "A" that is globally optimal, but ignored as too expensive initially.

Sub-optimal solutions can be used to lessen the greediness of the down-pass (and up-pass) methods. For example, as shown in FIG. 19, the assignment of preliminary sequence "A" is globally optimal, but ignored as too expensive initially. A set of sub-optimal solutions can be considered, in order to improve the efficiency of the method.

Figure 20:
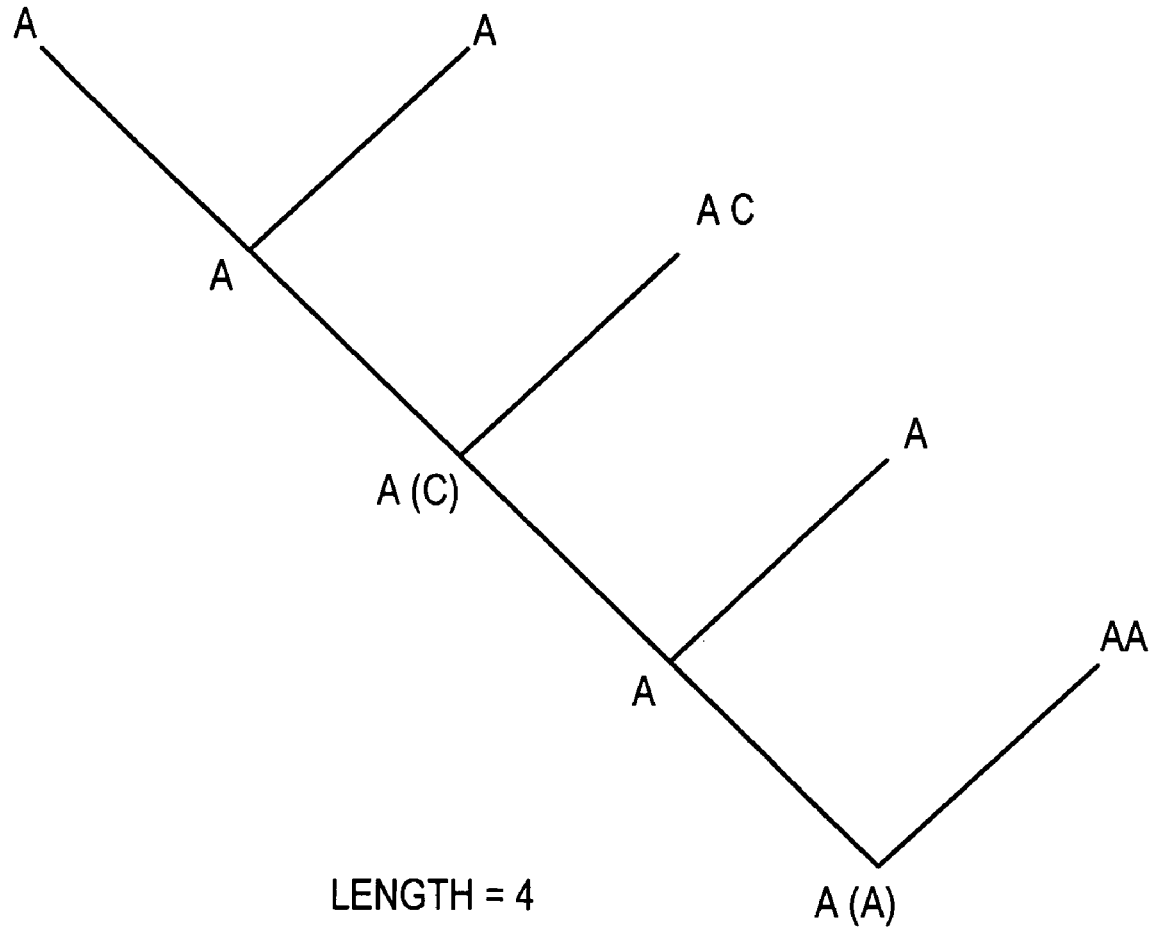
FIG. 20 illustrates a different rooting of sequence "A."

FIG. 19 and FIG. 20 show how rooting can affect the behavior of the down- and up-pass algorithms. Certain characters might well behave better (i.e. generate shorter cladogram lengths) given certain roots. Unfortunately, it is unlikely that these roots will be identical for all characters. However, a system of "virtual" roots can be erected with each character having its own "best" root, and then the OA procedure can be performed on that basis. The overall cladogram would then be more explicitly unrooted, and presented in a rooted fashion only at the end of the analysis.

In an embodiment where an up-pass optimization regime of the OA procedure would allow more than one possible nucleotides, one of the nucleotides is chosen (e.g., at random) and the OA procedure continues up the tree. This is done since these sequences are specific and too many ambiguities can lead to non-metricity. In such an embodiment, non-ambiguous sequences are generated which are consistent with at least some schemes of a phylogenetic relationship. Moreover, ntaxa—1 potentially unique hypothetic ancestral sequences accumulate at each iteration.

In certain embodiments of the present invention, solutions based on the reconstructed final sequences of the internal nodes can be approximated. Also, the number of sequences can be dynamically altered during analyses in order to increase the efficiency of the method.

Figure 22:
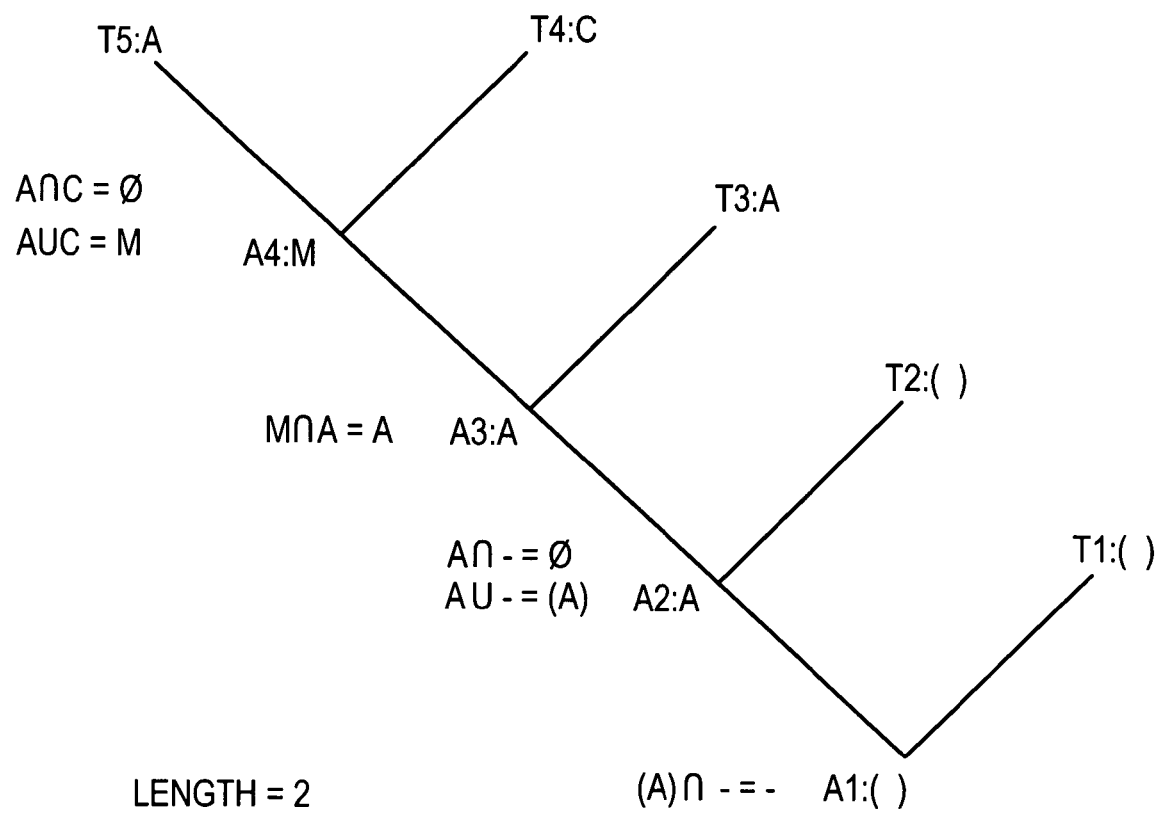
FIG. 22 shows a procedure whereby a candidate set of hypothetical sequences is defined.

In certain embodiments of the present invention, a tree such as the tree shown in FIG. 22 can be used to define the candidate set of hypothetical sequences. In such an embodiment, the tree could be used to calculate the wager trees.

FIG. 4 is an illustrative representation of the Wagner Tree used in the OA method. A plurality of original sequences 600 are shown. The OA method is used to generate possible sequences for each internal node 610. The sequences generated at each internal node 610 are then stored as a set of possible sequences 620, which will be used in the dynamic programming method (Step 210).

Figure 5:
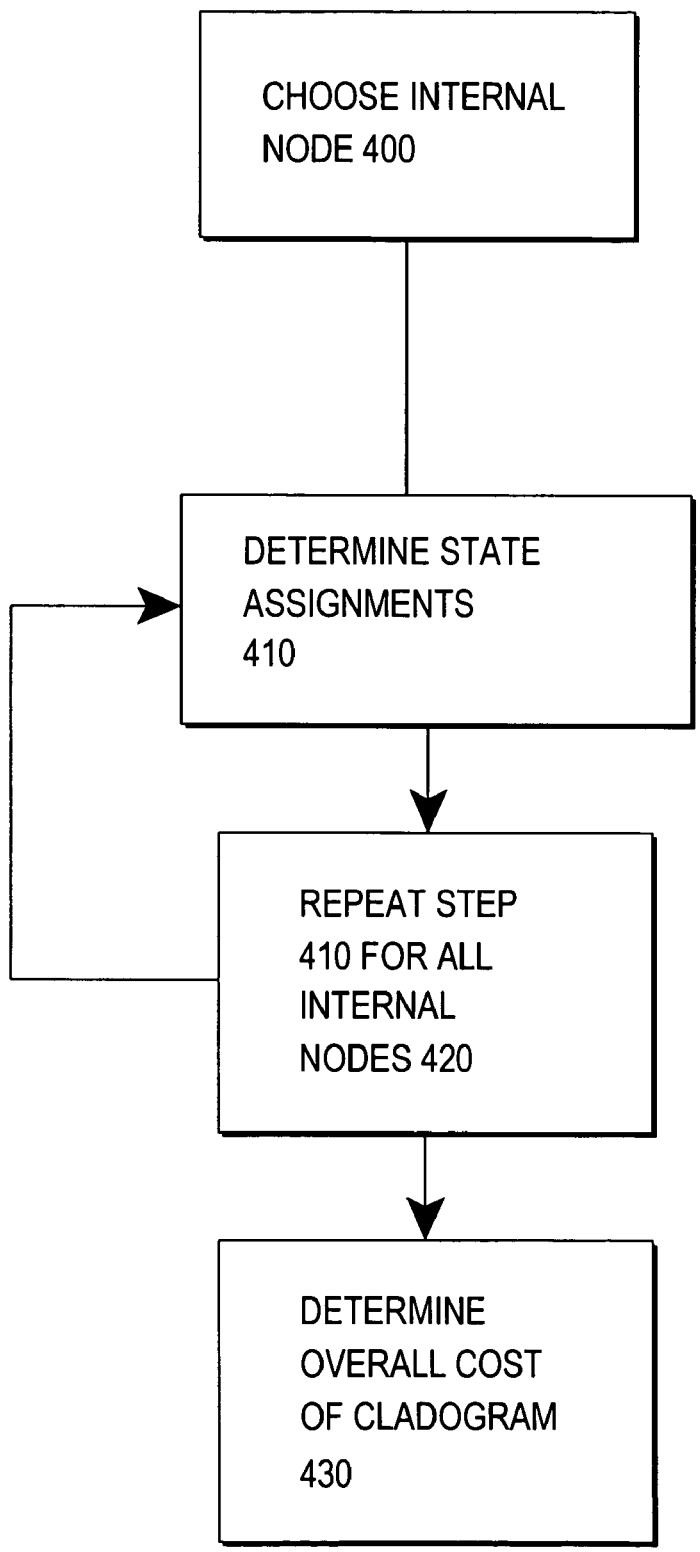
FIG. 5 shows a method for performing the "down-pass" that yields both preliminary character state assignments to the internal (i.e. ancestral) nodes and the cladogram length or cost on one of the Wagner Trees.

FIG. 5 shows a method for performing the "down-pass" in the OA method that yields both preliminary character state assignments to the internal (i.e. ancestral) nodes and the cladogram length or cost on one of the Wagner Trees.

Figure 21:
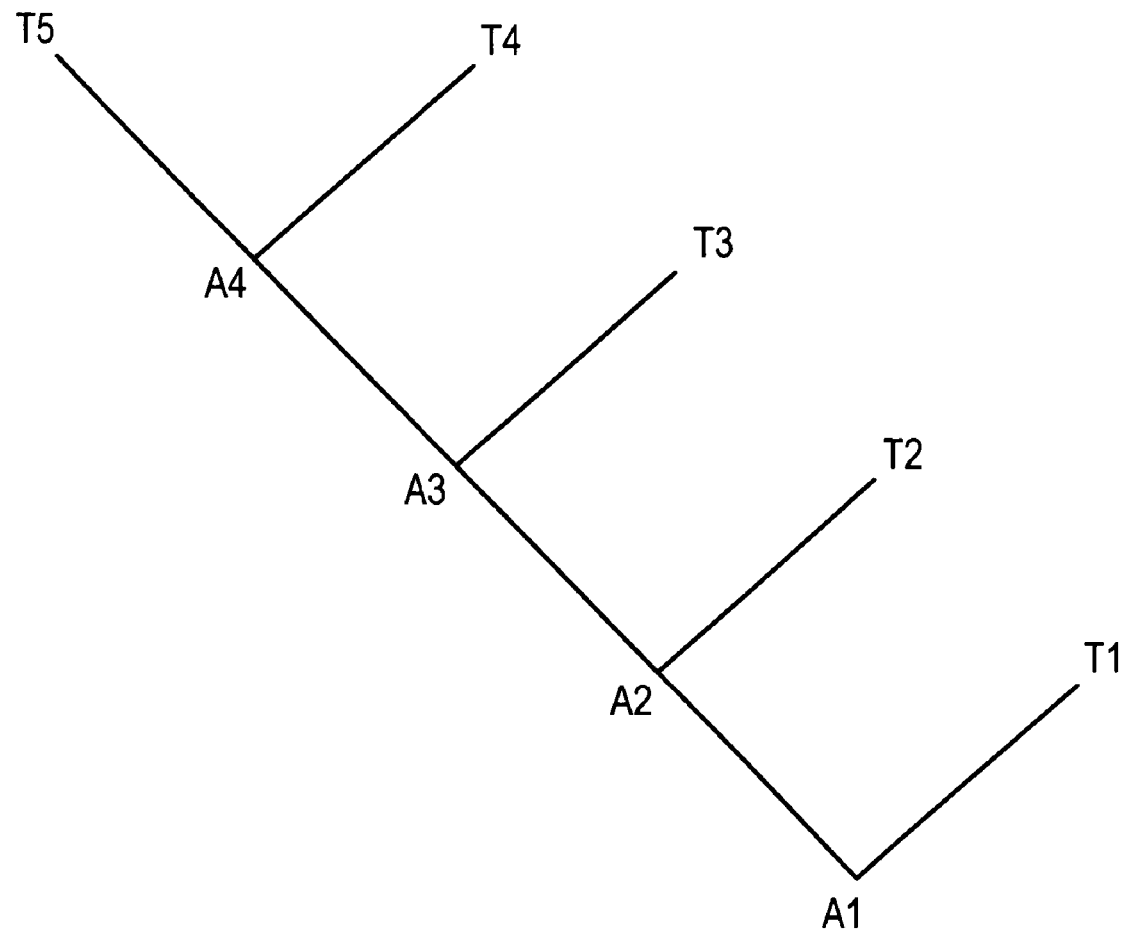
FIG. 21 illustrates an internal node whose two descendants are terminal taxa.

Whether the characters are morphological additive or non-additive characters, unordered or matrix molecular variants (J. S. Farris, *A method for computing Wagner trees*, Syst. Zool. 34:21–34 (1970); W. M. Fitch, *Toward defining the course of evolution: minimum*, Syst. Zool. 20:406–416 (1971) & D. D. Sankoff & P. Rousseau, *Locating the vertices of a Steiner tree in arbitrary space*, Math. Prog. 9:240–246 (1975).) the basic operation begins by choosing an internal node whose two descendants are terminal taxa (e.g., T1 and T2 shown in FIG. 21) (Step 400). The down-pass character state assignments (preliminary of node A4) are determined from the two descendants and minimize the amount of change between the ancestor and its two descendants (T1, T2, and A4) (Step 410). Step 410 is repeated until all the internal nodes have been visited (A4–A1) using the relevant ancestral preliminary states as descendants for more basal ancestors (e.g. A4 and T2 for A3) (Step 420). The overall cost of the cladogram is then determine by summing of the costs incurred in determining each ancestral sequence (Step 430). OA procedures can differ in the determination of the ancestral state reconstructions and how their costs are determined. For example, in an embodiment of the present invention where simple binary or non-additive multistate characters are used, union and intersection operations are performed on the descendant character states. In such an embodiment, if the two descendants states agree (identical) or have common states (non-empty intersection), no cost is incurred and the nodal reconstructed state is the identical or overlapping states in the two descendants. However, if the descendant states disagree (empty intersection), the ancestral state receives the union of the descendant states and the cost of that reconstruction is increased by one (e.g. T1 {A} and T2 {C} to yield A4 {M} (shown in FIG. 21).

Figure 23:
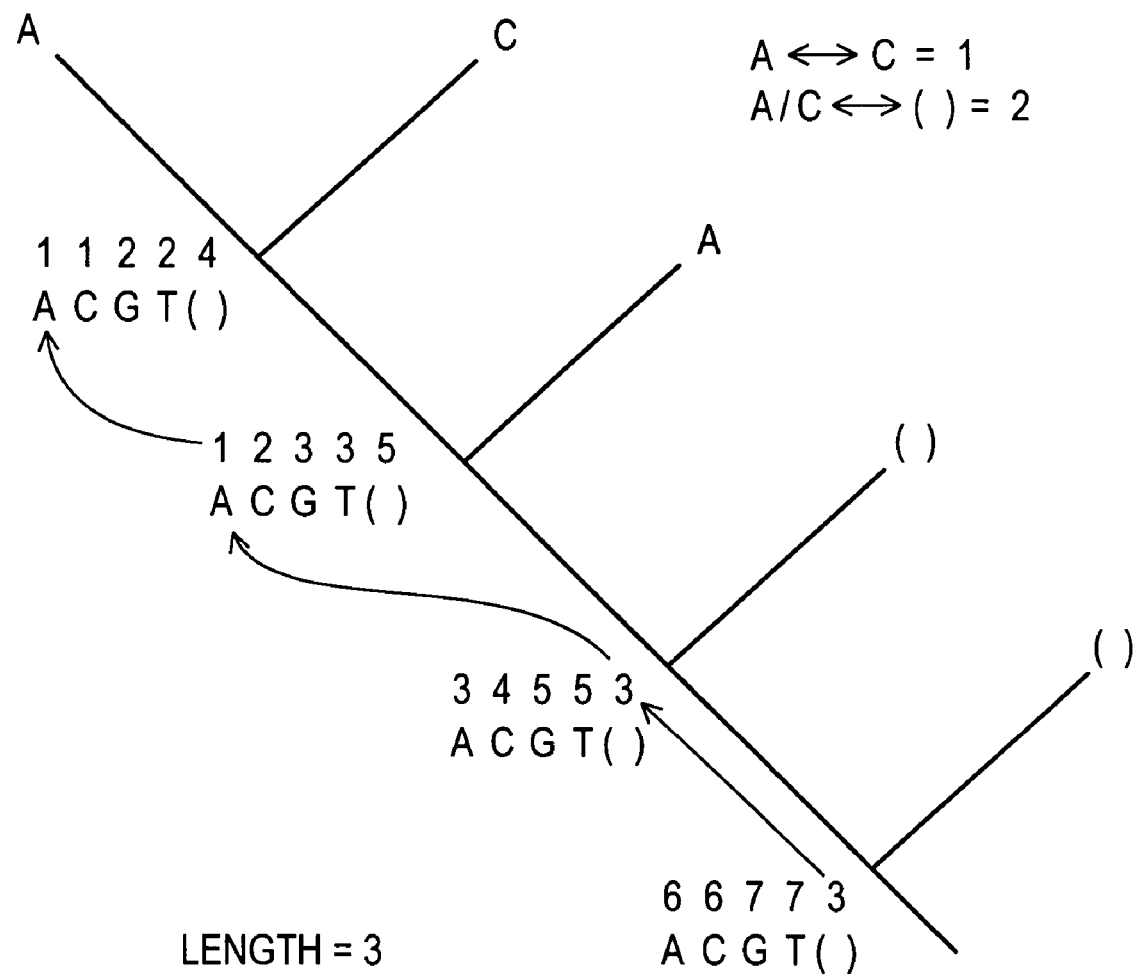
FIG. 23 illustrates a topology where multiple states are linked by arbitrary (but metric) transformations.

In an embodiment according to the present invention where multiple states are linked by arbitrary (but metric) transformation, cost matrices can be determined by trying (at least implicitly) all possible states at all internal nodes and choosing the combination which yields the most parsimonious result (Shown in FIG. 23). In such an embodiment, cost of the determination of ancestral nodes at each node it summed to get the length of the entire cladogram for that character. By way of comparison, for the Sankoff procedure to function, all possible internal states must be known and defined a priori, which allows them all to be considered. In most situations (e.g. nucleotide data), this is straight forward, with only five (A, C, G, T, and gap) states possible. Methods have been proposed where the number of possible states can be arbitrarily large (W. C. Wheeler, *Fixed Character States and the Optimization of Molecular Sequence Data*, Cladistics 15: 379–386 (1999).), but these character states can still be optimized via the same process as for the five states of nucleotide data. OA generalizes this procedure-allowing the creation and destruction of characters, but employs a heuristic character optimization algorithm (Heuristic Sankoff Cost) to make the calculations tractable.

Figure 6:
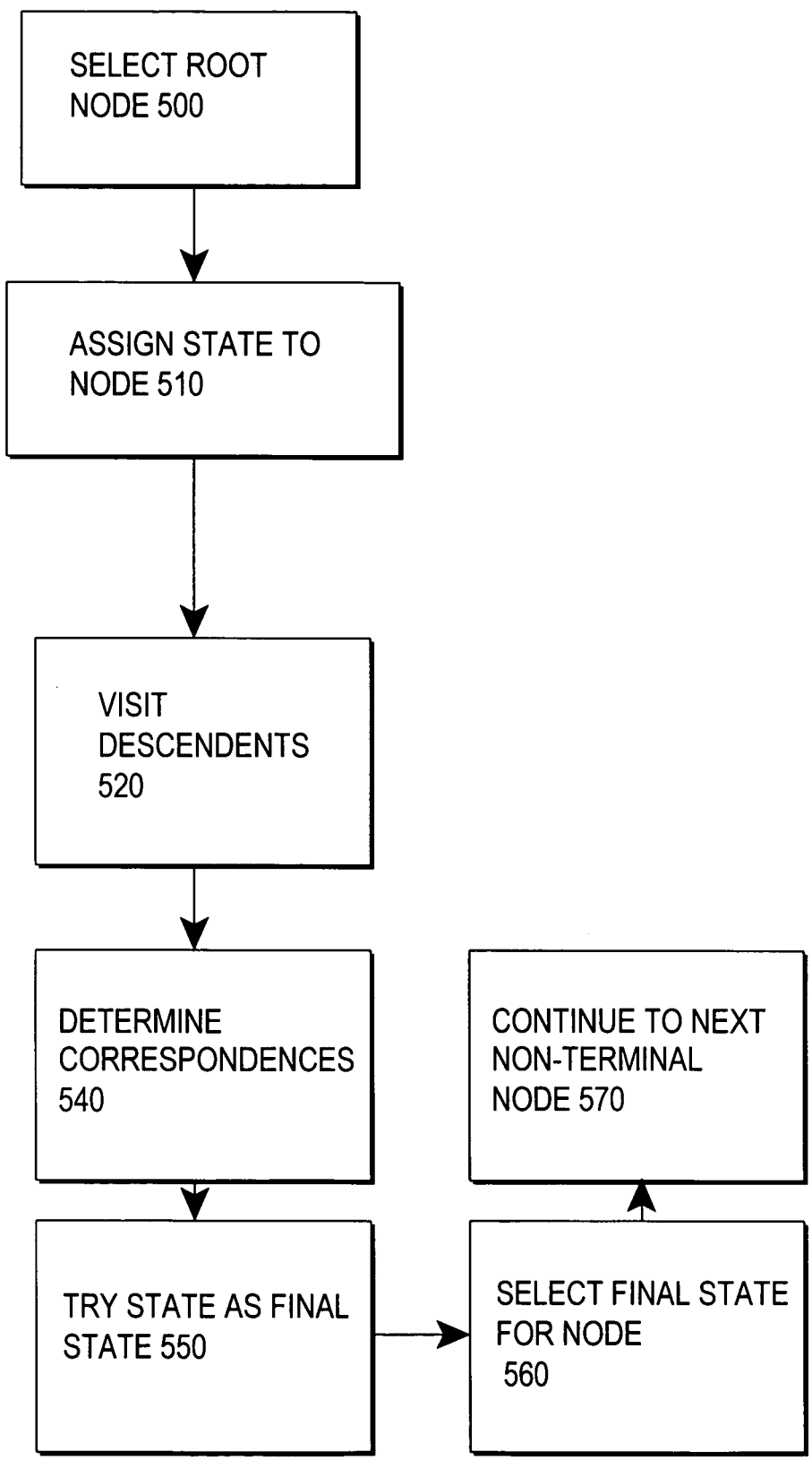
FIG. 6 shows a method for performing the "up-pass" optimization of the OA.

FIG. 6 shows a method for performing the "up-pass" optimization of the OA procedure. In order to reconstruct a parsimonious set of character states at the internal (hypothetical) nodes, a second or up-pass is required. This process moves from the root of the cladogram "up" to the tips, incorporating the information from a node's ancestor as well as its descendants. As originally described (W. C. Wheeler, *Optimization Alignment: the end of multiple sequence alignment in phylogenetics*, Cladistics, 12:1–9 (1996).) the process is extremely simple, basically trying all possible states (based on the down-pass homologies) in turn and keeping those with the lowest cost.

The root node is selected (Step 500) The final states for the root node are simply assigned from the preliminary states or the final states of the outgroup taxon (Step 510), since it has no ancestor. The descendants of this node are then visited (Step 520). These nodes are the first ones with both descendants and ancestors. The preliminary homologies among the preliminary down-pass states and the two descendant sequences are known (saved) from the down-pass step (Step 530) and the correspondences with the final states of its ancestor are determined by the same NW-HSC process used in the down-pass (Step 540), but between the preliminary states of the node and the final states of its ancestor. For each position then, the two descendant and ancestral states are known. Each state is tried in turn as the final state (Step 550), and the most parsimonious set taken as the final state set for that node (Step 560. The process then moves on the next node (Step 570) until final state sets are determined for each non-terminal node. The final state sets for the terminals and the root node, are of course identical to the preliminary states.

Figure 7:
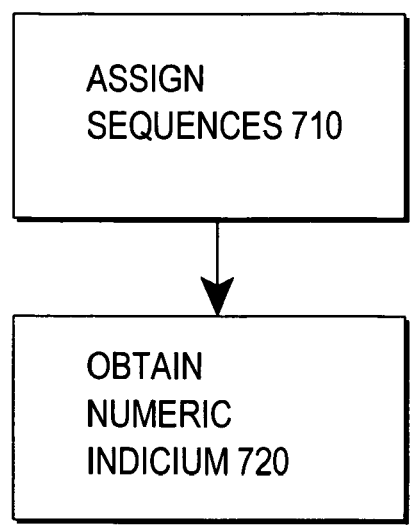
FIG. 7 shows a dynamic programing step in accordance with an embodiment of the present invention.
Figure 8:
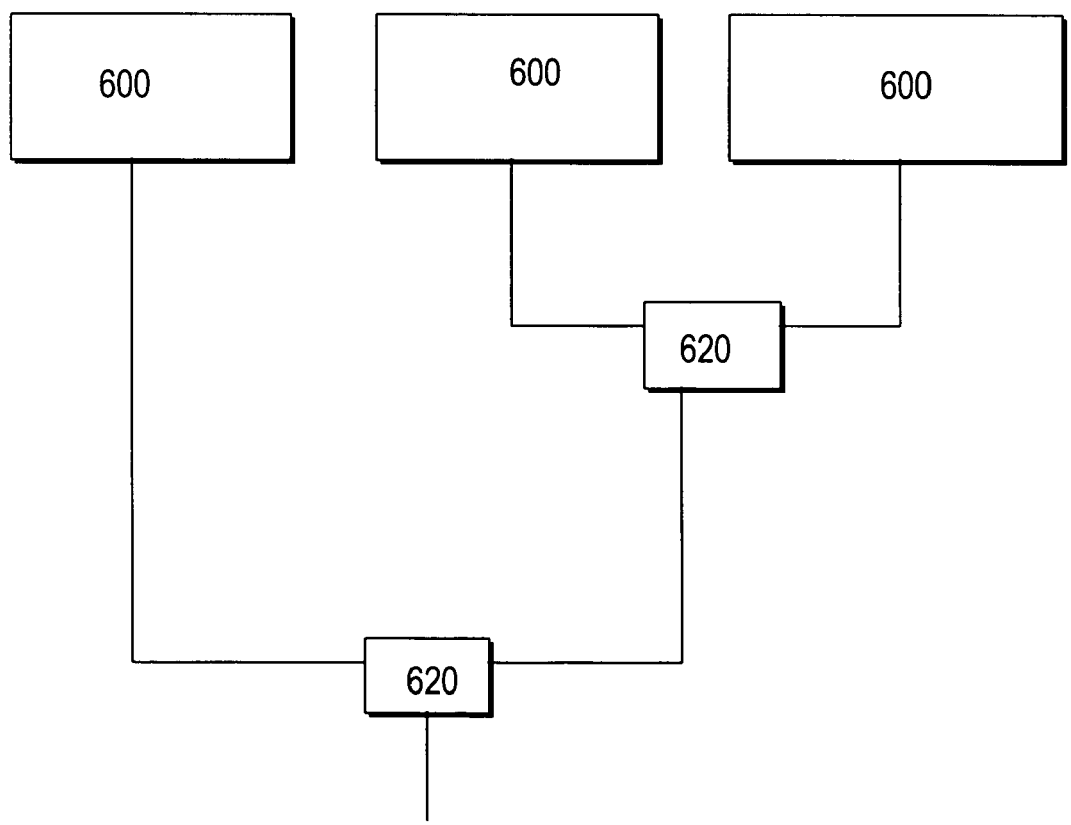
FIG. 8 shows an exemplary topology with a plurality of original states 600 and internal nodes 620.
Figure 12:
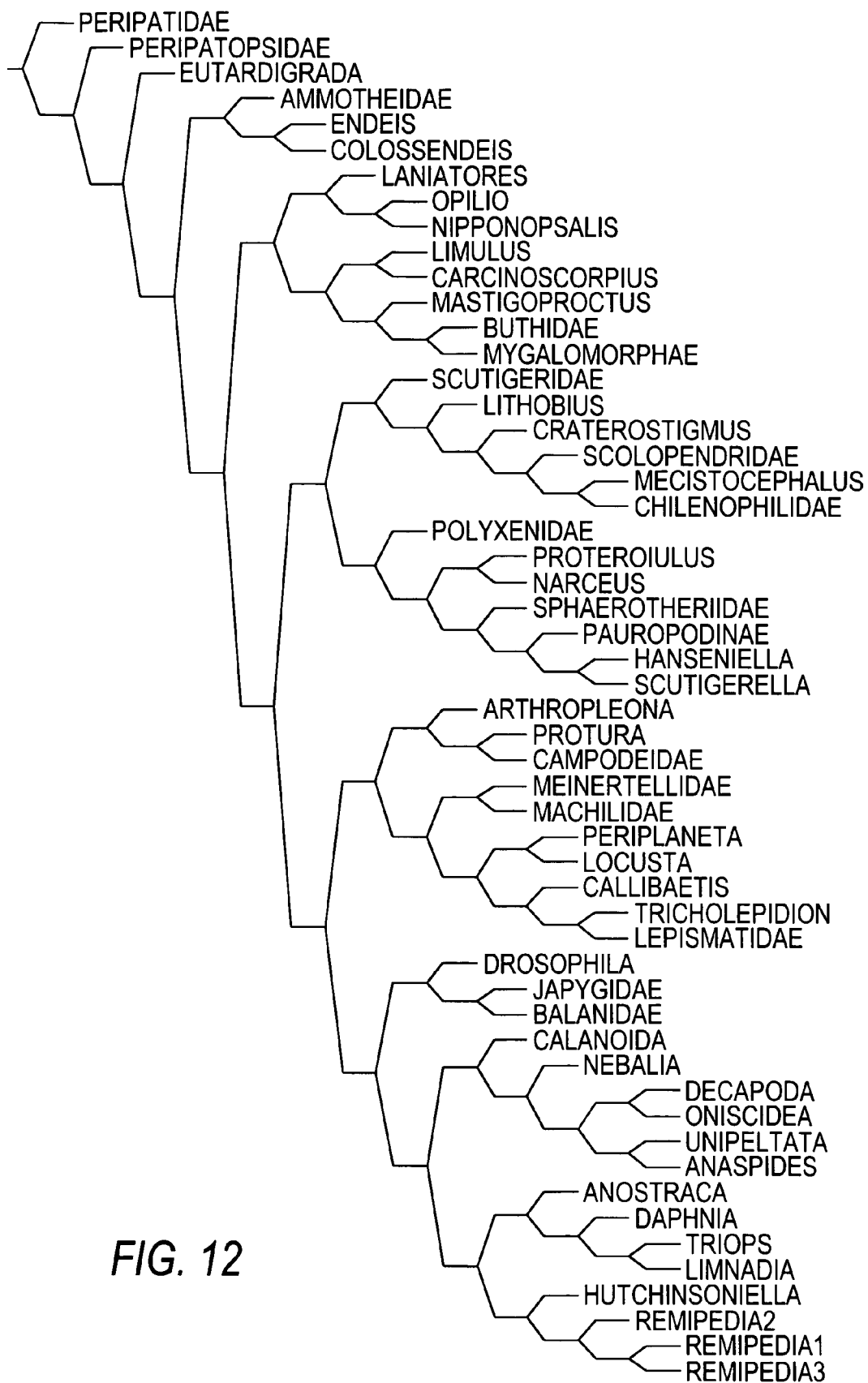
FIG. 12 shows a Cladogram of arthropod relationships of Giribet et al. (2001).
Figure 13:
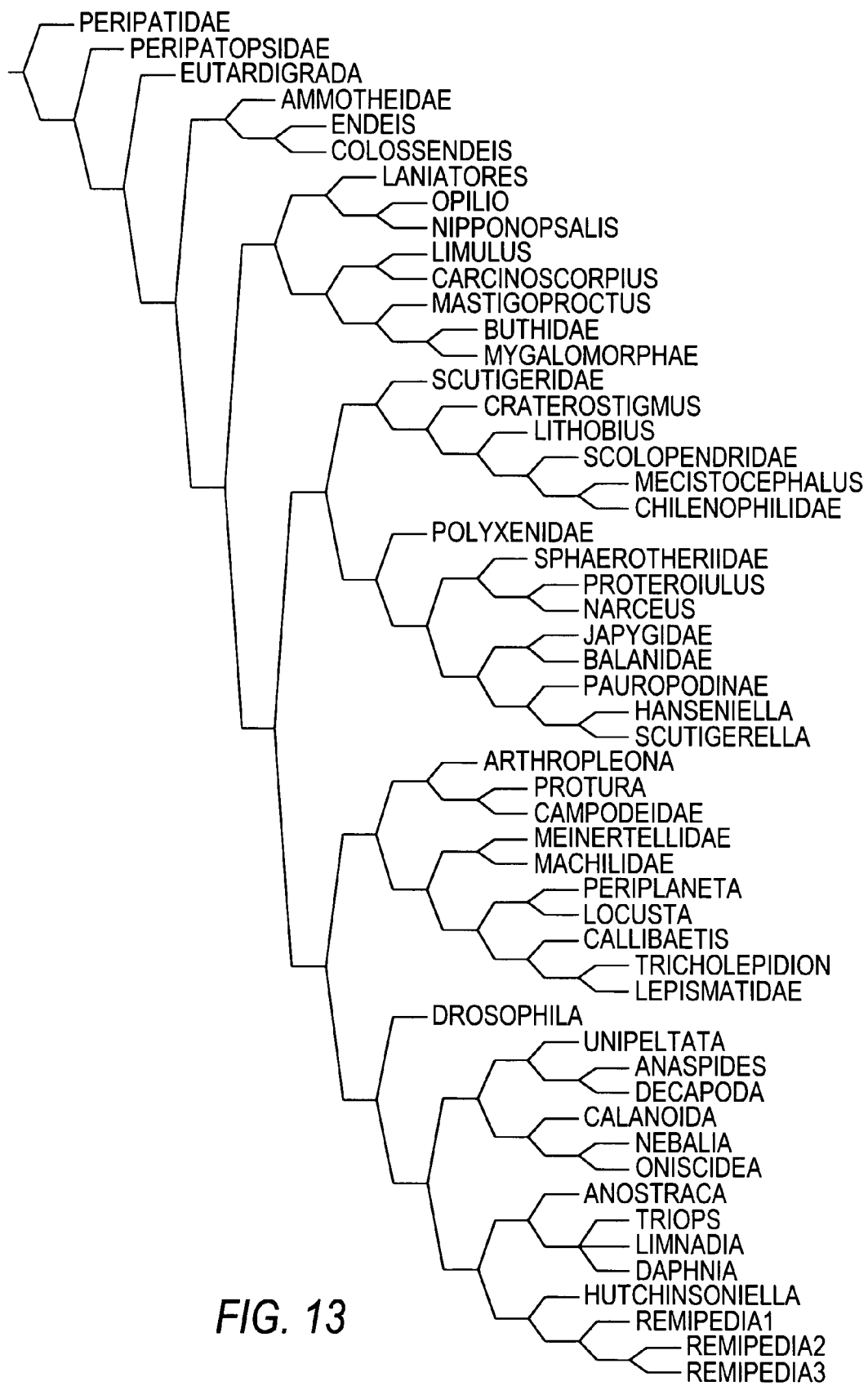
FIG. 13 shows the cladogram generated by the Search-based optimization in accordance with an embodiment of the present invention when performed on the Giribet et al. (2001) data.
Figure 14:
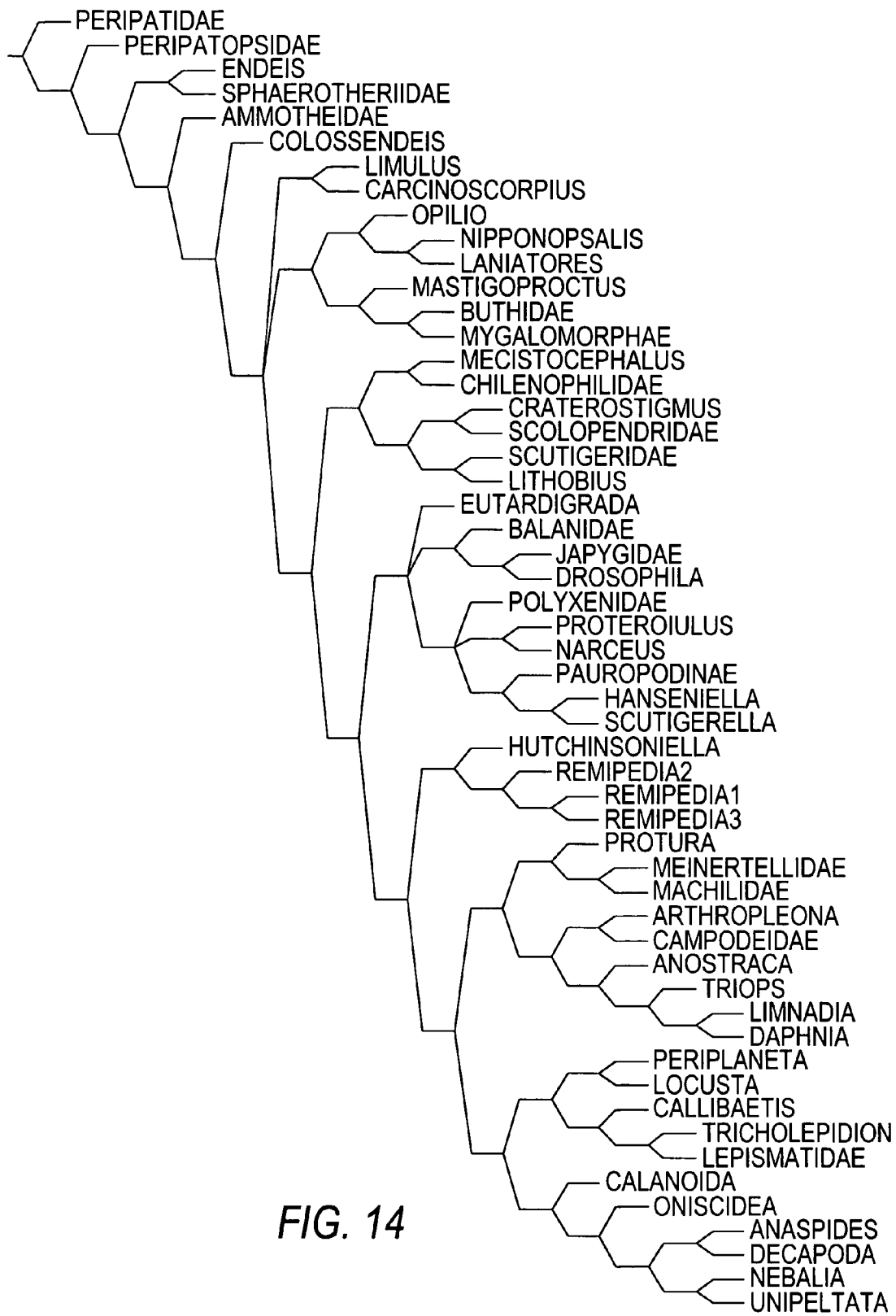
FIG. 14 shows the cladogram generated by the prior art fixed-states optimization technique when performed on the Giribet et al. (2001) data.

FIG. 7 shows the dynamic programing step according to an embodiment of the present invention. The possible sequences are assigned to the internal nodes of the topologies generated in Step 115 (Step 710). An exemplary topology with sequences is shown in FIG. 8. A numeric indicium is then calculated for each topology (Step 720). Preferably, the numeric indicium can be calculated by a Sankoff and Rousseau procedure.

The Sankoff and Rousseau procedure uses a matrix to calculate a hypothetical distance between sequences. The matrix assigns an edit cost to determine the distance between the particular characters of the sequences. If the sequences are composed of binary characters, there would be only two states and the single edit cost would be one step. If the sequences are prealigned nucleotide positions, there would be 5 states and a traditional Sankoff and Rousseau (D. D. Sankoff & P. Rousseau. *Locating the vertices of a Steiner tree in arbitrary space*, Math. Prog. 9:240–246 (1975).) matrix would specify all the possible transformations. Hence, this type of procedure is a generalization of other character types and can be applied to the character data generated by gene order studies with more states. In an embodiment of the present invention where the sequences are a set of nucleotides, the matrix can comprise the pairwise minimum edit costs between the sequences.

FIG. 8 shows an exemplary topology with a plurality of original sequences 600 and the set of possible sequences (which can be obtained from the previously generated Wagner trees) 620. The topology could, for example, have been generated by Step 115 and the possible sequences by Step 110 (both in FIG. 2). Step 140, which is the dynamic programing step, could be used on FIG. 8 to obtain a numeric indicium of merit. It should be noted that the set of possible sequences 620 were generated at the internal nodes of the Wagner tree shown in FIG. 4. However, it should be appreciated that other topologies are possible and that FIG. 8 only serves as an aid in understanding an embodiment according to the present invention.

FIG. 9 shows 9 sequences 400 (SEQ ID NO: 1–9) used to compare an embodiment of according to the present invention to other methods known in the art. In this example the 9 sequences 400 comprise nucleotides with lengths of 2 to 12 characters. In accordance with the search based optimization according to an embodiment of the present invention, potential internal sequences were generated with the computer program, POY (vers. 2.7; Gladstein and Wheeler, 1997) using the options "-nospr-notbr-maxtrees 1-seed-1-random 1-printhypanc-diagnose." A default indel cost of 2 and base substitution cost of 1 were used as well. POY then created a single random addition Wagner tree without any refinement such as SPR or TBR branch swapping. Ancestral sequences (e.g., cladograms) were saved each time and a "random" optimization regime was used to create non-ambiguous hypothetical ancestral sequences. These hypothetical ancestral sequences were kept each time and duplications removed. The first 100 unique sequences so generated are shown in FIG. 10.

Once defined, the potential sequence set was applied to cladogram diagnosis and searches. Without any additional states specified, so that the sequence set is limited to observed sequences, the shortest cladogram found had a cost of 44 weighted steps. With 100 additional sequences and branch-swapping tree refinement, the minimum cost cladogram had a length of 40 weighted steps. This minimum length was achieved at 61 additional sequences (for a states set of 70 including the 9 observed) and remained at 40 through states set sizes of 2000. This is shown in FIG. 11.

Applying the prior art CLUSTAL (1994, 1997), PHAST (Goloboff, 1996), and MALIGN (Wheeler and Gladstein, 1994, 1991) algorithms to the sequences of FIG. 9 generated cladograms of greater weighted lengths were generated than with an embodiment according to the present invention. Specifically, The CLUSTAL and PHAST algorithms generated a cladogram of weighted length 56, while the MALIGN and PHAST algorithms generated a cladogram of length 43. The data set generated by the optimization alignment (prior art) had a length of 40. This data set is the also shown in FIG. 11.

When a second sequence file was added which did not allow simultaneously minimal reconstructions, a greater difference between the weighted lengths of the cladograms was observed. Although each sequence file can yield a minimum length cladogram of 40 steps, together the minimum for search-based optimization (with the same 100 additional sequences) is 84. The prior art OA method yielded a cladogram of 86 weighted steps. By comparison, application of the prior art MALIGN and PHAST algorithms yielded a cladogram of 106 weighted steps. Application of the prior art CLUSTAL and PHAST algorithms yielded 120 weighted steps. Moreover, the cladogram length with no additional states (Fixed-States cladogram) had a length of 91 weighted steps. Clearly, the prior art OA method yielded shorter length cladograms than other methods; the search-based optimization cladogram in accordance with an embodiment of the present invention is 2% shorter than optimization alignment and over 20% shorter than the multiple alignment methods.

An embodiment of the present invention can also applied to a real data set regarding arthropod relationships. In their multilocus and morphology total evidence analysis of 54 arthropods taxa, Giribet et al. (2001) reported support for "Pancrustacea" grouping of insects and crustaceans. To do this, Giribet presented 303 morphological characters and 8 nuclear and mitochondrial loci. They analyzed their data with an Optimization Alignment. Also, their congruence-based sensitivity analysis favored a cladogram employing completely homogeneous weighting (indels=transversions=transitions) at 27375 steps (prior art OA method).

In order to prepare the set of potential ancestral sequences, a procedure similar to that used for the test case above was performed. For each locus, or fragment of a locus, 50 random addition Wagner trees were calculated using the OA method. No branch swapping was performed, sequence variation was optimized on the resulting cladogram, and final hypothetical ancestral sequences reconstructed. The optimized best results from searches of the individual loci (or fragments) and a combined run were then added. A total of 2756 hypothetical ancestral sequences were generated for each of the loci (some of which are shown in FIG. 10) (SEQ ID NO: 10). There was often considerable redundancy and the number of unique potential sequences varied greatly. The first 550 of these unique sequences were chosen as the potential state set (in addition to the observed sequences). The potential state set was then used in the subsequent search-based optimization analyses in accordance with an embodiment of the present invention.

The cladogram of Giribet et al, was diagnosed by other methods known in the art. For example, an original cladogram length of 27375 was recovered by an optimization alignment (shown in FIG. 12). However, a cladogram length of 24107 steps was recovered by using the search based optimization according to the present invention. A Fixed-states (prior art) yielded a cladogram length of 2696 steps. When a complete search was performed (using POY vers. 2.7-beta on 50 1 Ghz PIII processors in parallel) with the search based optimization according to an embodiment of the present invention, a length of 23408 new steps was found (shown in FIG. 13). This was a decrease in tree length of 17%. By comparison, a Fixed-states search resulted in a cladogram of length 26066 (shown in FIG. 14). This shows that for a given cladogram the search-based optimization according to an embodiment of the present invention is superior, and when coupled with another method it is even more efficient.

FIG. 16 (SEQ ID NO: 20–30) shows an input file for an embodiment according to the present invention. In certain embodiments of the present invention, the sequences can be stored in an input file. In the input file of FIG. 16, a plurality of taxa 100 are shown. Also shown are a plurality of nucleotide sequences 1120 as they relate to the taxa 100.

FIG. 17 shows the cladogram generated by an embodiment according to the present invention for the input file shown in FIG. 16. The taxa 1110 are shown as they relate to one another based on differences in the nucleotide sequences 1120.

FIG. 18 shows a GUI interface for an embodiment according to the present invention. An input window 1310, info window 1320, and output window 1330 are shown. The GUI interface comprises a matrix file field 1340. The matrix file field 1340 allows a user to specify a particular matrix to use during the dynamic programing step. An output file field 1350 is also present, which allows the user to specify a path for an output file. A first and second data file field 1360,1370 provide paths to files containing input sequences (e.g., genetic sequences).

In the preceding specification, the invention has been described with reference to specific exemplary embodiments thereof. It will, however, be evident that various modifications and changes may be made thereto without departing from the broader spirit and scope of the invention as set forth in the claims that follow. The specification and drawings are accordingly to be regarded in an illustrative manner rather than a restrictive sense.

What is claimed is:

1. A method for selecting a set of sequences, comprising the steps of:
    defining a set of sequences, each one of the sequences comprising one or more characters;
    evaluating a sub-set of the set of sequences with a dynamic programing method to obtain a numeric indicium of merit related to an ancestral tree;
    adding additional sequences into the sub-set of sequences;
    repeating the steps of defining, evaluating, and adding until the numeric indicia is substantially constant or there are no more additional sequences; and
    selecting one of the sub-set of sequences based on the numeric indicia.

2. The method as recited in claim 1 wherein the step of defining the set of sequences further comprises the steps of:
    inserting one or more sequences into a Wagner tree in an order;
    repeating the step of inserting with the order a different order from each prior order;
    comparing each of the sequences in each of the Wagner Trees; and
    selecting one of the Wagner Trees based on the comparison.

3. The method as recited in claim 2 wherein the order is a random order.

4. The method as recited in claim 2 wherein the Wagner Trees are cladograms.

5. The method as recited in claim 1 further comprising the step of generating the sequences prior to the step of defining the sequences.

6. The method as recited in claim 1 further comprising the step of transmitting the selected sub-set of sequences subsequent to the step of selecting.

7. The method as recited in claim 1 wherein the selected sub-set of sequences is represented by a cladogram.

8. The method as recited in claim 1 wherein the sub-set of sequences further comprise one or more nucleotides.

9. The method as recited in claim 1 wherein the sub-set of sequences further comprise one or more amino acids.

10. The method as recited in claim 1 wherein the step of evaluating further comprises constructing a cost matrix using the sub-set of sequences.

11. The method as recited in claim 10 wherein the matrix is a Sankoff and Rousseau matrix.

12. The method as recited in claim 1 further comprising repeating all the steps with a new set of sequences, the new set of sequences being generated using characteristics of the selected sub-set of sequences.

13. A method for selecting a set of sequences, comprising the steps of:
    (A) defining a set of sequences, each one of the sequences comprising one or more characters;
    (B) evaluating a sub-set of the set of sequences with a dynamic programing method to obtain a numeric indicia of merit related to an ancestral tree;
    (C) adding additional sequences into the sub-set of sequences;
    (D) repeating the steps of A, B and C until the numeric indicia is substantially constant or there are no more additional sequences; and
    (E) selecting one of the sub-set of sequences based on the numeric indicia.

14. The method as recited in claim 13 wherein the step of defining the set of sequences further comprises the steps of:
    (A) inserting one or more sequences into a Wagner tree in an order;
    (B) repeating step A with the order a different order from each prior order;
    (C) comparing each of the sequences in each of the Wagner Trees; and
    (D) selecting one of the Wagner Trees based on the comparison.

15. The method as recited in claim 14 wherein the order is a random order.

16. The method as recited in claim 13 further comprising the step of generating the set of sequences prior to Step A.

17. The method as recited in claim 13 further comprising the step of transmitting the selected sub-set of sequences subsequent to the step E.

18. The method as recited in claim 13 wherein the selected sub-set of sequences is represented by a cladogram.

19. The method as recited in claim 13 wherein the sub-set of sequences further comprise one or more nucleotides.

20. The method as recited in claim 13 wherein the sub-set of sequences further comprise one or more amino acids.

21. The method as recited in claim 13 wherein step B further comprises constructing a cost matrix using the sub-set of sequences.

22. The method as recited in claim 21 wherein the matrix is a Sankoff and Rousseau matrix.

23. The method as recited in claim 13 further comprising repeating all the steps with a new set of sequences, the new set of sequences being generated using characteristics of the selected sub-set of sequences.

24. A method for selecting a set of sequences comprising the steps of:
    defining a possible set of sequences from an original set of sequences, each one of the sequences comprising one or more characters, the possible set of sequences including the original set of sequences;
    iteratively evaluating a sub-set of the possible set of sequences with a dynamic programing method to obtain a numeric indicium of merit related to an ancestral tree; and
    selecting a sub-set of the possible set of sequences based on the numeric indicium.

25. The method as recited in claim 24 further comprises the step of repeating the step of evaluating until a stability based on the numeric indicia occurs or there are no longer any sets of sequences to evaluate.

26. The method as recited in claim 24 wherein the step of defining is performed by an optimization alignment.

27. The method as recited in claim 24 wherein the step of defining further comprises the steps of:
    generating one or more Wagner trees based on the original set of sequences; and extracting the internal nodes of the Wagner trees to form the set of possible sequences.

28. The method as recited in claim 27 further comprising the steps of:
    performing an up-pass the Wager Trees before extracting the internal nodes of the tree; and
    performing a down-pass on the Wagner Trees before extracting the internal nodes of the tree.

29. The method as recited in claim 28 wherein the steps of performing an up-pass and a down-pass further comprise applying multiple solutions.

30. The method as recited in claim 28 wherein the steps of performing an up-pass and a down-pass further comprise further comprise using sub-optimal solutions.

31. The method as recited in claim 27 further comprising assigning a virtual root to the Wagner tree.

32. The method as recited in claim 27 wherein each Wagner tree is generated in parallel.

33. The method as recited in claim 24 wherein the step of iteratively evaluating a sub-set of the possible set of sequences further comprises the steps of:

generating one or more topologies based on the original set of sequences, each one of the topologies comprising one or more internal states;

assigning the possible set of sequences to the internal states of the topologies; and obtaining the numeric indicium of merit from each of the tree topologies by a Sankoff and Rousseau procedure.

34. The method as recited in claim 33 wherein each topology is generated in parallel.

35. The method as recited in claim 24 further comprising the step of obtaining the sequences prior to the step of defining.

36. The method as recited in claim 24 further comprising the step of transmitting the selected sub-set of the possible set of sequences subsequent to the step of selecting.

37. The method as recited in claim 24 wherein the selected sub-set of the possible set of sequences represented by a cladogram.

38. The method as recited in claim 24 wherein the sub-set of sequences further comprise one or more nucleotides.

39. The method as recited in claim 24 wherein the sub-set of sequences further comprise one or more amino acids.

40. The method as recited in claim 24 further comprising the step of obtaining the sequences from one or more cancerous cells prior to the step of defining.

* * * * *

SEQUENCE LISTING

<160> NUMBER OF SEQ ID NOS: 44

<210> SEQ ID NO 1
<211> LENGTH: 10
<212> TYPE: DNA
<213> ORGANISM: Artificial
<220> FEATURE:
<223> OTHER INFORMATION: Comparison Sequence

<400> SEQUENCE: 1
atatatatat                                                              10

<210> SEQ ID NO 2
<211> LENGTH: 12
<212> TYPE: DNA
<213> ORGANISM: Artificial
<220> FEATURE:
<223> OTHER INFORMATION: Comparison Sequence

<400> SEQUENCE: 2
atagatacta aa                                                           12

<210> SEQ ID NO 3
<211> LENGTH: 11
<212> TYPE: DNA
<213> ORGANISM: Artificial
<220> FEATURE:
<223> OTHER INFORMATION: Comparison Sequence

<400> SEQUENCE: 3
ttgacatagc a                                                            11

<210> SEQ ID NO 4
<211> LENGTH: 10
<212> TYPE: DNA
<213> ORGANISM: Artificial
<220> FEATURE:
<223> OTHER INFORMATION: Candidate Ancestral Sequence

<400> SEQUENCE: 4
ttagatagca                                                              10

<210> SEQ ID NO 5
<211> LENGTH: 10
<212> TYPE: DNA
<213> ORGANISM: Artificial
<220> FEATURE:
<223> OTHER INFORMATION: Candidate Ancestral Sequence

<400> SEQUENCE: 5
atagatataa                                                              10

<210> SEQ ID NO 6
<211> LENGTH: 10
<212> TYPE: DNA
<213> ORGANISM: Artificial
<220> FEATURE:
<223> OTHER INFORMATION: Candidate Ancestral Sequence

<400> SEQUENCE: 6
ttatatatca                                                              10

<210> SEQ ID NO 7
<211> LENGTH: 10

```
<212> TYPE: DNA
<213> ORGANISM: Artificial
<220> FEATURE:
<223> OTHER INFORMATION: Candidate Ancestral Sequence

<400> SEQUENCE: 7
atatatataa                                                          10

<210> SEQ ID NO 8
<211> LENGTH: 12
<212> TYPE: DNA
<213> ORGANISM: Artificial
<220> FEATURE:
<223> OTHER INFORMATION: Candidate Ancestral Sequence

<400> SEQUENCE: 8
atatatacta aa                                                       12

<210> SEQ ID NO 9
<211> LENGTH: 11
<212> TYPE: DNA
<213> ORGANISM: Artificial
<220> FEATURE:
<223> OTHER INFORMATION: Candidate Ancestral Sequence

<400> SEQUENCE: 9
ttgacataga a                                                        11

<210> SEQ ID NO 10
<211> LENGTH: 10
<212> TYPE: DNA
<213> ORGANISM: Artificial
<220> FEATURE:
<223> OTHER INFORMATION: Candidate Ancestral Sequence

<400> SEQUENCE: 10
ttagatatat                                                          10

<210> SEQ ID NO 11
<211> LENGTH: 10
<212> TYPE: DNA
<213> ORGANISM: Artificial
<220> FEATURE:
<223> OTHER INFORMATION: Candidate Ancestral Sequence

<400> SEQUENCE: 11
atagatatat                                                          10

<210> SEQ ID NO 12
<211> LENGTH: 10
<212> TYPE: DNA
<213> ORGANISM: Artificial
<220> FEATURE:
<223> OTHER INFORMATION: Candidate Ancestral Sequence

<400> SEQUENCE: 12
atagatatca                                                          10

<210> SEQ ID NO 13
<211> LENGTH: 10
<212> TYPE: DNA
<213> ORGANISM: Artificial
<220> FEATURE:
<223> OTHER INFORMATION: Candidate Ancestral Sequence

<400> SEQUENCE: 13
```

```
atatatatac                                                    10

<210> SEQ ID NO 14
<211> LENGTH: 11
<212> TYPE: DNA
<213> ORGANISM: Artificial
<220> FEATURE:
<223> OTHER INFORMATION: Candidate Ancestral Sequence

<400> SEQUENCE: 14
atagatacta a                                                  11

<210> SEQ ID NO 15
<211> LENGTH: 10
<212> TYPE: DNA
<213> ORGANISM: Artificial
<220> FEATURE:
<223> OTHER INFORMATION: Candidate Ancestral Sequence

<400> SEQUENCE: 15
atacatatat                                                    10

<210> SEQ ID NO 16
<211> LENGTH: 11
<212> TYPE: DNA
<213> ORGANISM: Artificial
<220> FEATURE:
<223> OTHER INFORMATION: Candidate Ancestral Sequence

<400> SEQUENCE: 16
atgatactaa a                                                  11

<210> SEQ ID NO 17
<211> LENGTH: 11
<212> TYPE: DNA
<213> ORGANISM: Artificial
<220> FEATURE:
<223> OTHER INFORMATION: Candidate Ancestral Sequence

<400> SEQUENCE: 17
atgatataaa a                                                  11

<210> SEQ ID NO 18
<211> LENGTH: 10
<212> TYPE: DNA
<213> ORGANISM: Artificial
<220> FEATURE:
<223> OTHER INFORMATION: Candidate Ancestral Sequence

<400> SEQUENCE: 18
atatatatat                                                    10

<210> SEQ ID NO 19
<211> LENGTH: 10
<212> TYPE: DNA
<213> ORGANISM: Artificial
<220> FEATURE:
<223> OTHER INFORMATION: Candidate Ancestral Sequence

<400> SEQUENCE: 19
ttacatatct                                                    10

<210> SEQ ID NO 20
<211> LENGTH: 10
<212> TYPE: DNA
<213> ORGANISM: Artificial
```

```
<220> FEATURE:
<223> OTHER INFORMATION: Candidate Ancestral Sequence

<400> SEQUENCE: 20
ttagatatct                                                          10

<210> SEQ ID NO 21
<211> LENGTH: 11
<212> TYPE: DNA
<213> ORGANISM: Artificial
<220> FEATURE:
<223> OTHER INFORMATION: Candidate Ancestral Sequence

<400> SEQUENCE: 21
atgatataga a                                                        11

<210> SEQ ID NO 22
<211> LENGTH: 11
<212> TYPE: DNA
<213> ORGANISM: Artificial
<220> FEATURE:
<223> OTHER INFORMATION: Candidate Ancestral Sequence

<400> SEQUENCE: 22
ttgatattaa a                                                        11

<210> SEQ ID NO 23
<211> LENGTH: 12
<212> TYPE: DNA
<213> ORGANISM: Artificial
<220> FEATURE:
<223> OTHER INFORMATION: Candidate Ancestral Sequence

<400> SEQUENCE: 23
atagatacta aa                                                       12

<210> SEQ ID NO 24
<211> LENGTH: 11
<212> TYPE: DNA
<213> ORGANISM: Artificial
<220> FEATURE:
<223> OTHER INFORMATION: Candidate Ancestral Sequence

<400> SEQUENCE: 24
atgatatata a                                                        11

<210> SEQ ID NO 25
<211> LENGTH: 11
<212> TYPE: DNA
<213> ORGANISM: Artificial
<220> FEATURE:
<223> OTHER INFORMATION: Candidate Ancestral Sequence

<400> SEQUENCE: 25
tagatataac a                                                        11

<210> SEQ ID NO 26
<211> LENGTH: 10
<212> TYPE: DNA
<213> ORGANISM: Artificial
<220> FEATURE:
<223> OTHER INFORMATION: Candidate Ancestral Sequence

<400> SEQUENCE: 26
agagatataa                                                          10
```

```
<210> SEQ ID NO 27
<211> LENGTH: 10
<212> TYPE: DNA
<213> ORGANISM: Artificial
<220> FEATURE:
<223> OTHER INFORMATION: Candidate Ancestral Sequence

<400> SEQUENCE: 27
tgagatatca                                                          10

<210> SEQ ID NO 28
<211> LENGTH: 11
<212> TYPE: DNA
<213> ORGANISM: Artificial
<220> FEATURE:
<223> OTHER INFORMATION: Candidate Ancestral Sequence

<400> SEQUENCE: 28
atgatatatc a                                                        11

<210> SEQ ID NO 29
<211> LENGTH: 11
<212> TYPE: DNA
<213> ORGANISM: Artificial
<220> FEATURE:
<223> OTHER INFORMATION: Candidate Ancestral Sequence

<400> SEQUENCE: 29
tagatattaa a                                                        11

<210> SEQ ID NO 30
<211> LENGTH: 10
<212> TYPE: DNA
<213> ORGANISM: Artificial
<220> FEATURE:
<223> OTHER INFORMATION: Candidate Ancestral Sequence

<400> SEQUENCE: 30
atacatataa                                                          10

<210> SEQ ID NO 31
<211> LENGTH: 12
<212> TYPE: DNA
<213> ORGANISM: Artificial
<220> FEATURE:
<223> OTHER INFORMATION: Sequence from Cladogram diagnosis

<400> SEQUENCE: 31
atagatacta aa                                                       12

<210> SEQ ID NO 32
<211> LENGTH: 11
<212> TYPE: DNA
<213> ORGANISM: Artificial
<220> FEATURE:
<223> OTHER INFORMATION: Sequence from Cladogram Diagnosis

<400> SEQUENCE: 32
ttgacatagc a                                                        11

<210> SEQ ID NO 33
<211> LENGTH: 10
<212> TYPE: DNA
<213> ORGANISM: Artificial
<220> FEATURE:
<223> OTHER INFORMATION: Sequence from Cladogram Diagnosis
```

```
<400> SEQUENCE: 33
atatatatat                                                                  10

<210> SEQ ID NO 34
<211> LENGTH: 143
<212> TYPE: DNA
<213> ORGANISM: Americhernus

<400> SEQUENCE: 34
tcgagcctcc aatgatacgt tgaaaggcgt ttatcgttgg ggccgacagc gcgtcgtggg           60
ctcggttggc cttaaaaagc tgatcgggtt ctccggcaat tttactttga aaaaattagg          120
gtgctcaaag caggcctggt gcc                                                  143

<210> SEQ ID NO 35
<211> LENGTH: 143
<212> TYPE: DNA
<213> ORGANISM: Chanbria

<400> SEQUENCE: 35
tctagactgg tggtccgcct ctggtggtta ctacctggcc taaacaattt gccggttttc           60
ccttggtgct cttcaccgag tgtcttgggg gactggtacg tttactttga agaaactaga          120
gtgctcaaag caggcgtaac gcc                                                  143

<210> SEQ ID NO 36
<211> LENGTH: 143
<212> TYPE: DNA
<213> ORGANISM: Gea

<400> SEQUENCE: 36
tccggccgga cgggtccgcc taccggtggt tactgttcgc tgccgagctt caggggccg            60 ctgtcgatga tcttcatcgg ttatcttccg taaccctcac gtttactttg aaaaaattag          120
agtgctcaaa gcagcgcgac gcc                                                  143

<210> SEQ ID NO 37
<211> LENGTH: 142
<212> TYPE: DNA
<213> ORGANISM: Hypochilus

<400> SEQUENCE: 37
tccagacggg cggtccgcct aacggtggtt actgcctggc ctgaacaacc agccggtttc           60
cctagatgat cttcattgat tgtcttgggt gaccggcacg tttactttga aaaaattaga          120
gtgctcaaag cagcgtgacg cc                                                   142

<210> SEQ ID NO 38
<211> LENGTH: 142
<212> TYPE: DNA
<213> ORGANISM: Thelichoris

<400> SEQUENCE: 38
tccagacggg cggtccgcct aacggtggtt actgcctggc ctgaacagcc agccggtttc           60
cctagatgat ctttaccggt tgtcttgggt gaccggcacg tttactttga aaaaattaga          120
gtgctcaaag caggctgacg cc                                                   142

<210> SEQ ID NO 39
<211> LENGTH: 142
<212> TYPE: DNA
```

<213> ORGANISM: Amblypygid

<400> SEQUENCE: 39

| | | |
|---|---|---|
| tccagactgg cggtccgcct agcggcgagt actgtcaggc ctgaacatgg cgccggtttt | 60 |
| ccttggttct ctttactgag tgtcttgggc gaccggcacg tttactttga aaaaattaga | 120 |
| gtgctcaaag caggctgtcg cc | 142 |

<210> SEQ ID NO 40
<211> LENGTH: 144
<212> TYPE: DNA
<213> ORGANISM: Mastigoproctus

<400> SEQUENCE: 40

| | | |
|---|---|---|
| tccagacggg tggtccaccg cccggtggct actgcccggc ctgaacaatc tcgccggttt | 60 |
| tccttgattc tcttcaccga gtgtcttggg tgaccggcac gttttacttt gaaaaaatta | 120 |
| gagtgcttaa agcagcgtaa cgcc | 144 |

<210> SEQ ID NO 41
<211> LENGTH: 145
<212> TYPE: DNA
<213> ORGANISM: Rhiphicephalus

<400> SEQUENCE: 41

| | | |
|---|---|---|
| tccagacgag tagtgcatct acccgatgct acggctcgga ctgaacatca tgccggttct | 60 |
| ttcttggtgc acttcattgt gtgcctcgag atggccggtg cttttacttt gaaaaaatta | 120 |
| gagtgctcaa cgcaggcgag tcgcc | 145 |

<210> SEQ ID NO 42
<211> LENGTH: 144
<212> TYPE: DNA
<213> ORGANISM: Vonones

<400> SEQUENCE: 42

| | | |
|---|---|---|
| tcgaggctgg cggtccgcct acaggcggtc actgccagta ctcaacatcc tgccggtttt | 60 |
| cccttggtgc tcttcgctga gtgtctcggg tggccggcac gtttactttg aaaaaattag | 120 |
| agtgctcaaa gcaggcgcgt agcc | 144 |

<210> SEQ ID NO 43
<211> LENGTH: 141
<212> TYPE: DNA
<213> ORGANISM: Centruoides

<400> SEQUENCE: 43

| | | |
|---|---|---|
| tccagacaag cggtccaccc gcggtggtta ctgtttggac tggacgtttg gccggattcc | 60 |
| tttgatgctc tttgccgagt gtcttgggtg tccggcacgt ttactttgaa aaattagag | 120 |
| tgctcaaagc agcgtaccgc c | 141 |

<210> SEQ ID NO 44
<211> LENGTH: 142
<212> TYPE: DNA
<213> ORGANISM: Hadrurus

<400> SEQUENCE: 44

| | | |
|---|---|---|
| tccggactgt cggtccgccg caagcttact ggcaggaccg gacgtctagc cggactctct | 60 |
| cgtatcctct tcaccgggtg tcttgggtgt ccggcaattt tactttgaaa aattagagt | 120 |
| gctcaaagca gcgcgatccg cc | 142 |